(12) United States Patent
Arnold et al.

(10) Patent No.: US 12,285,341 B2
(45) Date of Patent: Apr. 29, 2025

(54) VERTEBRAL BODY REPLACEMENT

(71) Applicant: NuVasive, Inc., San Diego, CA (US)

(72) Inventors: Benjamin Arnold, San Diego, CA (US); Rich Mueller, Carlsbad, CA (US); William Smith, Las Vegas, NV (US); Sharath Bellary, Cumberland, MD (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 18/330,428

(22) Filed: Jun. 7, 2023

(65) Prior Publication Data

US 2023/0310174 A1    Oct. 5, 2023

Related U.S. Application Data

(63) Continuation of application No. 16/533,189, filed on Aug. 6, 2019, now Pat. No. 11,712,344, which is a
(Continued)

(51) Int. Cl.
*A61F 2/44* (2006.01)
*A61F 2/28* (2006.01)
(Continued)

(52) U.S. Cl.
CPC ............. *A61F 2/4465* (2013.01); *A61F 2/28* (2013.01); *A61F 2/44* (2013.01); *A61F 2/4455* (2013.01); *A61F 2/447* (2013.01); *A61F 2/4611* (2013.01); *A61F 2002/2835* (2013.01); *A61F 2002/30235* (2013.01); *A61F 2002/30393* (2013.01); *A61F 2002/30395* (2013.01); *A61F 2002/30405* (2013.01); *A61F 2002/30433* (2013.01); *A61F 2002/305* (2013.01); *A61F 2002/30507* (2013.01); *A61F 2002/3055* (2013.01); *A61F 2002/30556* (2013.01); *A61F 2002/30579* (2013.01); *A61F 2002/30593* (2013.01); *A61F 2002/30601* (2013.01); *A61F 2002/30772* (2013.01); *A61F 2002/30777* (2013.01); *A61F 2002/30779* (2013.01); *A61F 2002/30785* (2013.01); *A61F 2002/30789* (2013.01); *A61F 2002/30904* (2013.01); *A61F 2002/4622* (2013.01); *A61F 2002/4627* (2013.01); *A61F 2002/4628* (2013.01); *A61F 2310/00017* (2013.01); *A61F 2310/00023* (2013.01)

(58) Field of Classification Search
CPC ............................ A61F 2/4455; A61F 2/4611
See application file for complete search history.

(56) References Cited

U.S. PATENT DOCUMENTS 4,657,550 A * 4/1987 Daher ...................... A61F 2/44
                                                            623/17.11
5,458,641 A * 10/1995 Ramirez Jimenez ..... A61F 2/44
                                                            606/247
(Continued)

*Primary Examiner* — David W Bates

(57) ABSTRACT

The present invention involves a system and methods for assembling and implanting a vertebral body implant. The vertebral body implant includes, but is not necessarily limited to, an expandable core body and endplates that can be attached at both ends. Endplates of various shapes, sizes and angles are attachable to the expandable core so that a suitable vertebral body implant can be implanted between vertebrae.

12 Claims, 26 Drawing Sheets

Related U.S. Application Data continuation of application No. 15/498,296, filed on Apr. 26, 2017, now Pat. No. 10,413,421, which is a continuation of application No. 14/744,470, filed on Jun. 19, 2015, now Pat. No. 9,636,233, which is a continuation of application No. 13/964,836, filed on Aug. 12, 2013, now abandoned, which is a continuation of application No. 12/661,206, filed on Mar. 12, 2010, now Pat. No. 9,387,090.

(60) Provisional application No. 61/260,375, filed on Nov. 11, 2009, provisional application No. 61/159,792, filed on Mar. 12, 2009.

(51) Int. Cl.
*A61F 2/46* (2006.01)
*A61F 2/30* (2006.01)

(56) References Cited

U.S. PATENT DOCUMENTS

| | | | | |
|---|---|---|---|---|
| 5,702,455 | A * | 12/1997 | Saggar | A61F 2/44 623/17.15 |
| 6,866,682 | B1 * | 3/2005 | An | A61F 2/44 623/17.11 |
| 7,758,648 | B2 * | 7/2010 | Castleman | A61F 2/4611 623/17.11 |
| 2002/0082695 | A1 * | 6/2002 | Neumann | A61F 2/44 623/17.11 |
| 2004/0186569 | A1 * | 9/2004 | Berry | A61F 2/4465 623/17.11 |
| 2006/0058877 | A1 * | 3/2006 | Gutlin | A61F 2/44 623/17.11 |
| 2006/0084975 | A1 * | 4/2006 | Berry | A61F 2/4611 606/53 |
| 2006/0100710 | A1 * | 5/2006 | Gutlin | A61F 2/44 623/17.15 |
| 2007/0028710 | A1 * | 2/2007 | Kraus | A61F 2/4611 74/400 |
| 2007/0255410 | A1 * | 11/2007 | Dickson | A61F 2/4611 623/17.11 |
| 2010/0094424 | A1 * | 4/2010 | Woodburn | A61F 2/44 623/17.16 |
| 2019/0358055 | A1 | 11/2019 | Arnold et al. | |

* cited by examiner

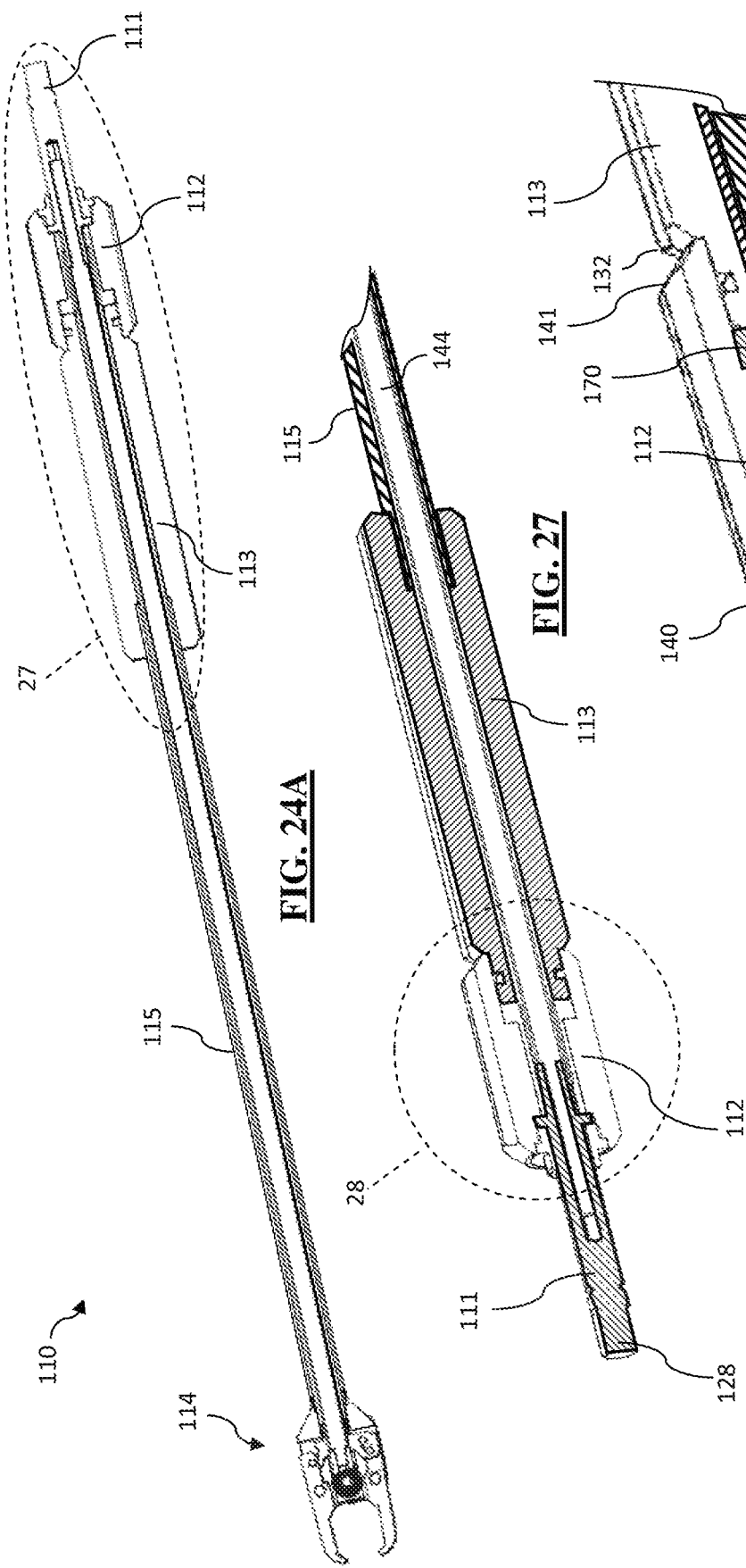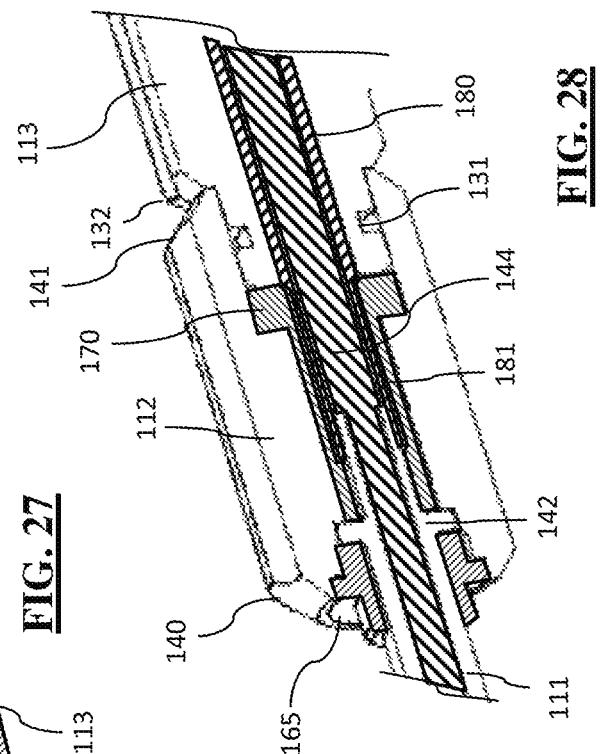

VERTEBRAL BODY REPLACEMENT

CROSS-REFERENCE TO RELATED APPLICATIONS

This application is a continuation of U.S. patent application Ser. No. 16/533,189, filed on Aug. 6, 2019, which is a continuation of U.S. patent application Ser. No. 15/498,296 (now U.S. Pat. No. 10,413,421), filed on Apr. 26, 2017, which is a continuation of U.S. patent application Ser. No. 14/744,470 (now U.S. Pat. No. 9,636,233), filed on Jun. 19, 2015, which is a continuation of U.S. patent application Ser. No. 13/964,836 filed on Aug. 12, 2013, which is a continuation of U.S. patent application Ser. No. 12/661,206 (now U.S. Pat. No. 9,387,090), filed on Mar. 12, 2010, which claims the benefit of priority from U.S. Provisional Patent Application Nos. 61/159,792, filed on Mar. 12, 2009, and 61/260,375, filed on Nov. 11, 2009. The entire contents of these previous related applications are each hereby expressly incorporated by reference into this disclosure.

FIELD

The present application relates generally to spinal implants and methods for replacing at least a portion of one or more vertebral bodies of a spine.

BACKGROUND

The spine is formed of a column of vertebra that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the pelvic region of the vertebral column. These fused vertebrae consist of the sacral and coccygeal region of the vertebral column.

The main functions of the spine are to provide skeletal support and protect the spinal cord. Even slight disruptions to either the intervertebral discs or vertebrae can result in serious discomfort due to compression of nerve fibers either within the spinal cord or extending from the spinal cord. If a disruption to the spine becomes severe enough, damage to a nerve or part of the spinal cord may occur and can result in partial to total loss of bodily functions (e.g. walking, talking, and breathing). Therefore, it is of great interest and concern to be able to both correct and prevent any ailments of the spine.

Trauma to the spine (e.g. car accident, sports injury) can cause fracturing of one or more vertebrae. Certain diseases affecting the spine (e.g. tumors, osteoporosis) can cause degeneration of the spine. Both trauma and degeneration may result in severe disruption to the spine. In these circumstances, the complete removal of one or more vertebrae may be required. If one or more vertebrae are removed, a replacement support system must be implanted in order to protect the spinal cord and maintain, or improve, the structure and integrity of the spine.

The present invention is directed at overcoming, or at least improving upon, disadvantages of the prior art.

BRIEF DESCRIPTION OF THE DRAWINGS

FIGS. 24A-B are a cross section view of the expanding tool of FIG. 23 taken along line 24-24 of FIG. 23;

FIG. 27 is a partial view of the expanding tool taken from partial view area 27 of FIG. 24;

FIG. 28 is a partial view of the expanding tool taken from partial view area 28 of FIG. 27;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as a compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The expandable vertebral body replacement disclosed herein boasts a variety of inventive features and components that warrant patent protection, both individually and in combination.

Figure 1:
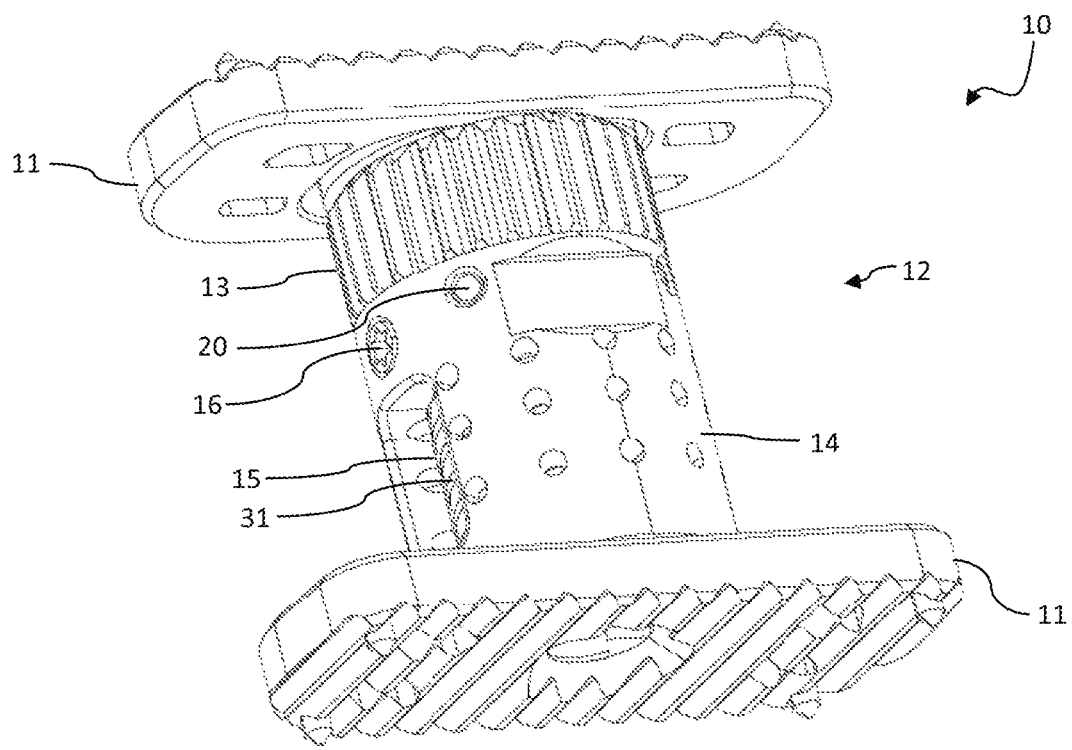
FIG. 1 is a perspective view of one example of a vertebral body implant assembly, according to one embodiment of the present invention.
Figure 2:
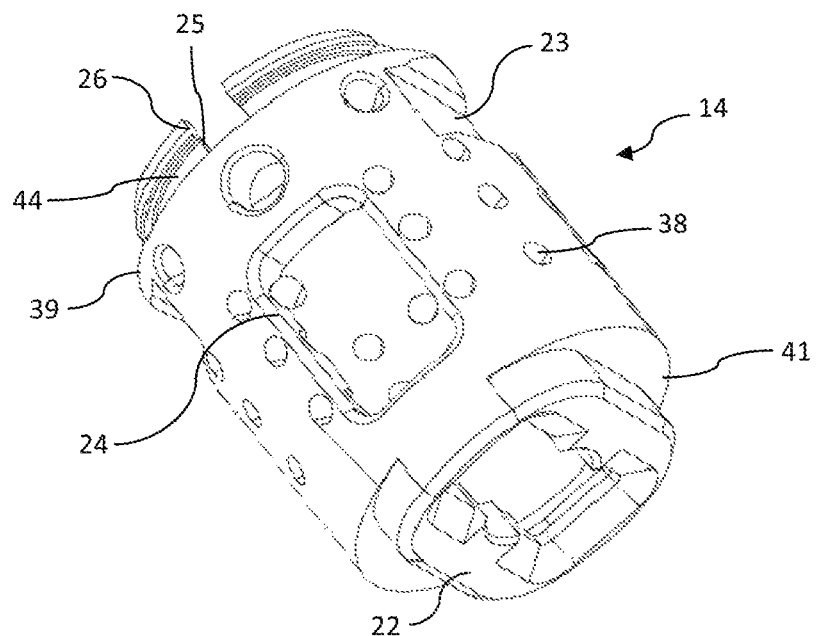
FIG. 2 is a perspective view of an outer tubular core forming part of the implant assembly of FIG. 1.
Figure 3:
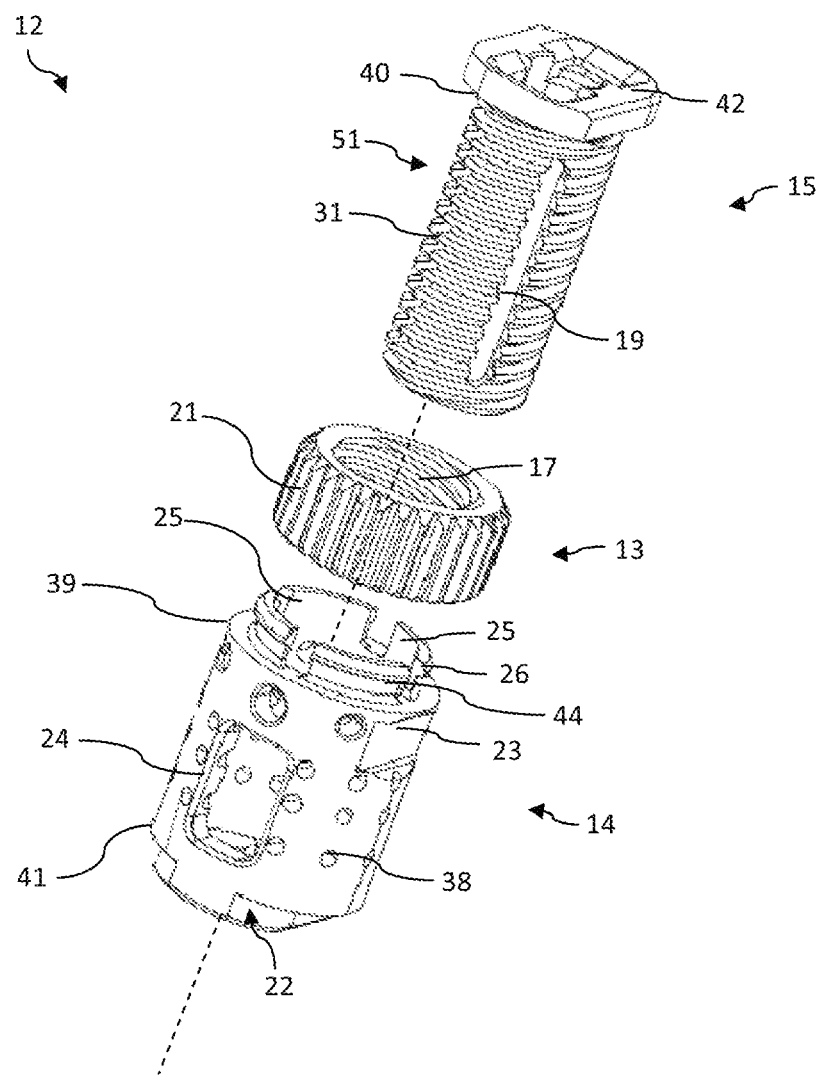
FIG. 3 is an exploded view of the core expanding body forming part of the implant assembly of FIG. 1.
Figure 4:
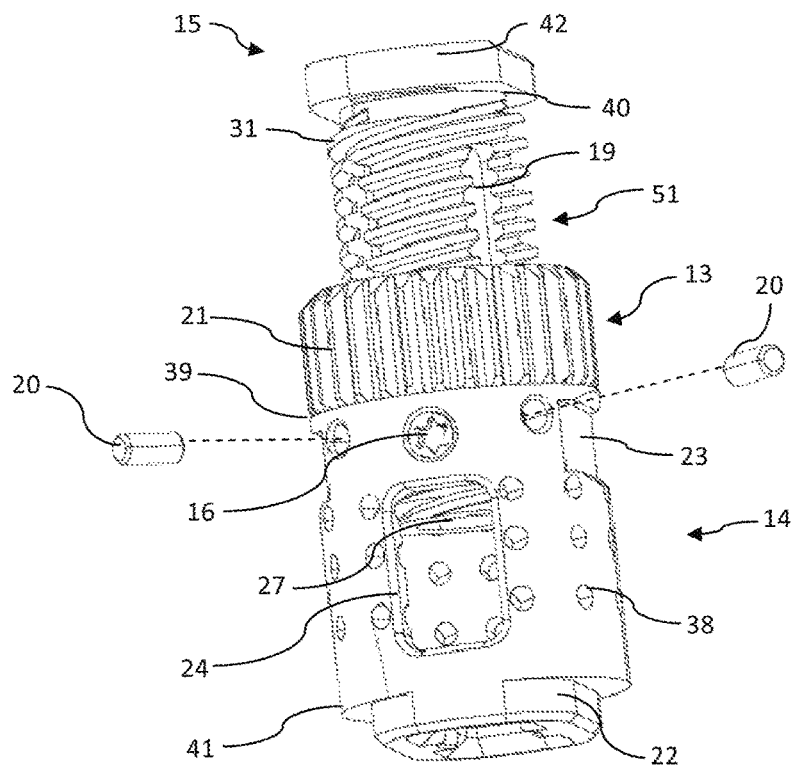
FIG. 4 is a partially exploded view directed at illustrating the guide pin and guide track interaction of the implant assembly of FIG. 1.

FIG. 1 illustrates an example of a vertebral body implant assembly 10 according to a first embodiment of the present invention. The vertebral body implant assembly 10 includes endplates 11 fixed at the superior and inferior ends of a tubular core expanding body 12 wherein the expandable implant can be customized to accommodate various needs by attaching from a selection of different endplates. The customization of the expandable tubular core can be done moments before implant of the expandable vertebral body replacement, which gives the benefit of customizing the implant based on expected and unexpected circumstances and conditions of the surrounding vertebral bodies.

The core expanding body 12 includes an adjustment ring 13, an outer tubular core 14, an inner tubular core 15, one or more guide pins 20, and one or more set screws 16. As will be explained in greater detail below, the vertebral body implant assembly 10 of the present invention may be inserted into a space left by the removal of at least part of one or more vertebra in order to maintain a desired spacing between the remaining vertebrae and to stabilize the affected spinal segments. To do so, the vertebral body implant assembly 10 is placed, preferably in a collapsed state, in the space between the remaining superior and inferior vertebral bodies. Rotation of the adjustment ring 13, which is fixed at one end of the outer tubular core 14 of the core expanding body 12, results in the expansion of the core expanding body 12 due to the outer tubular core 14 and inner tubular core 15 moving in opposite directions along their central axis. Expansion of the core expanding body 12 may be continued until the desired spacing between the vertebral bodies is achieved. Once the desired spacing is reached, a set screw 16 in the wall of the outer tubular core 14 is engaged into the exterior threads 31 of the inner tubular core 15 to secure the expanded position of the vertebral body implant assembly 10 and prevent further height alterations of the vertebral body implant assembly 10.

Referring to FIGS. 2-9, the outer tubular core 14 includes indented slots 23, a plurality of holes 38, an opening 24, a first end 39, a second end 41, a plurality of flanges 25 with a distal step 26 forming a groove 44, and an endplate attachment feature 22. Indented slots 23 on the exterior wall of the outer tubular core 14 allow for the anti-rotational attachment of the expanding tool, described below. The plurality of holes 38 in the wall of the outer tubular core 14 allow the transport of blood and nutrients through the core expanding body 12 once implanted, which assists in new bone growth between the remaining vertebra. The relatively large opening 24 in the side of the outer tubular core 14 allows the placement of additional bone growth promoting material to be added once the vertebral body implant assembly 10 has been positioned in the body and expanded to a desired height. A plurality of flanges 25 with a distal step 26 extend from the first end 39 of the outer tubular core 14 and function to secure the attachment of the adjustment ring 13 to the first end 39.

Figure 5:
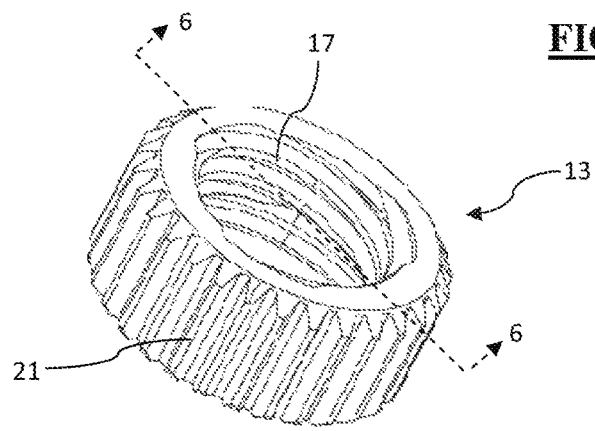
FIG. 5 is a perspective view of the adjustment ring forming part of the implant assembly of FIG. 1.
Figure 6:
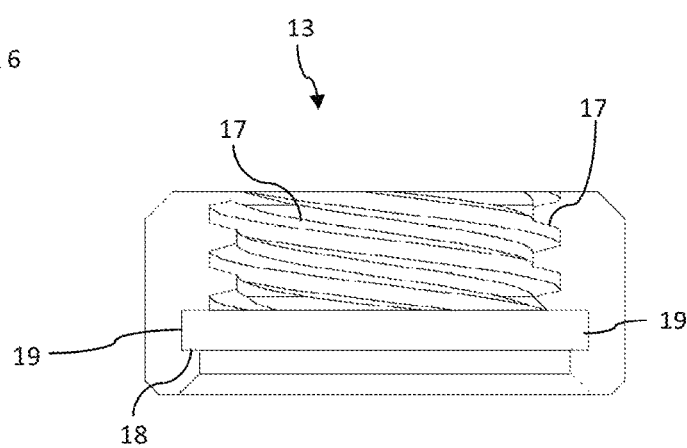
FIG. 6 is a cross section view of the adjustment ring of FIG. 5 taken along line 6-6 of FIG. 5.
Figure 7:
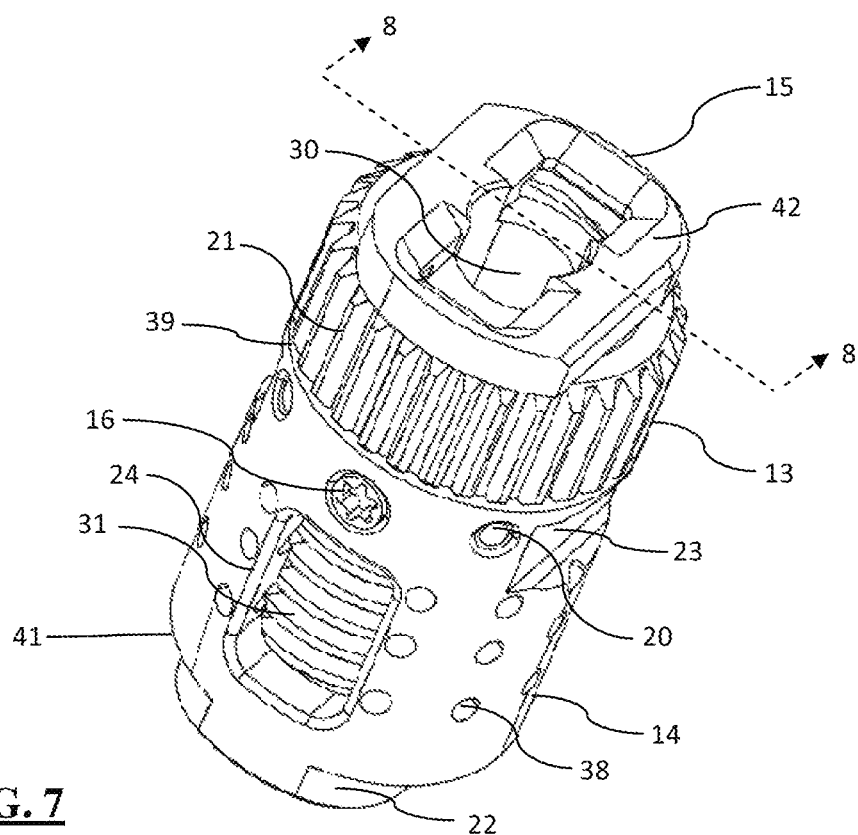
FIG. 7 is a perspective view of the core expanding body forming part of the implant assembly of FIG. 1.
Figure 8A:
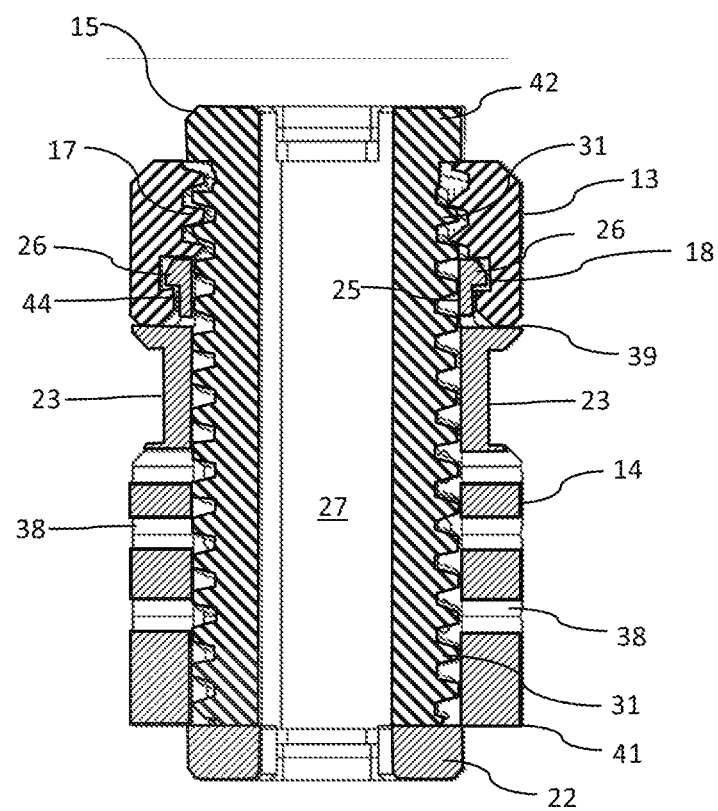
FIG. 8A is a cross section view of the core expanding body of FIG. 7 taken along line 8-8 of FIG. 7.
Figure 8B:
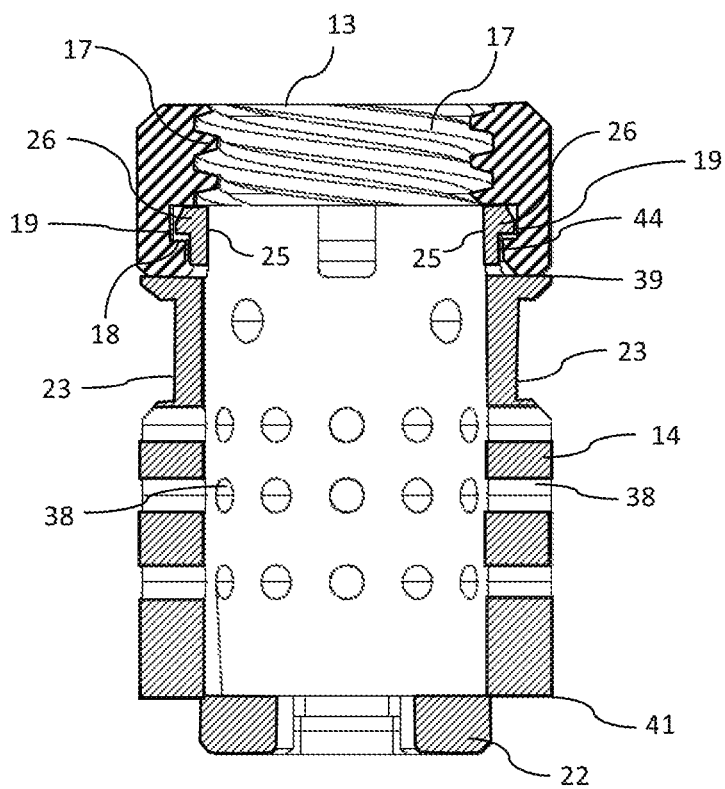
FIG. 8B is a cross section view of the adjustment ring and outer tubular core of the core expanding body of FIG. 7 taken along line 8-8 of FIG. 7.

The adjustment ring 13, shown by way of example in FIGS. 5 and 6, includes external features 21, internal threads 17, and an annular under-step 18 forming a groove 19. When assembled, the annular under-step 18 of adjustment ring 13 engages in the groove 41 of the core expanding body 12 and the distal step 26 engages in the groove 19 of the adjustment ring 13, longitudinally fixing the adjustment ring 13 and core expanding body 12 together while permitting rotational movement therebetween. External features 21 on the adjustment ring 13 are configured to engage a combination inserter/expansion tool which may be operated to rotate adjustment ring 13 to expand core expanding body 12. The internal threads 17 of the adjustment ring 13 engage with the external threads 31 of the inner tubular core 15 so that as the adjustment ring 13 rotates, it acts as a nut and forces the linear translation of the inner tubular core 15 along its central axis. The longitudinal fixation of the outer tubular core 14 to the adjustment ring 13 ensures the relative displacement of the inner tubular core 15 to the outer tubular core 14 as the adjustment ring 13 rotates.

Figure 9:
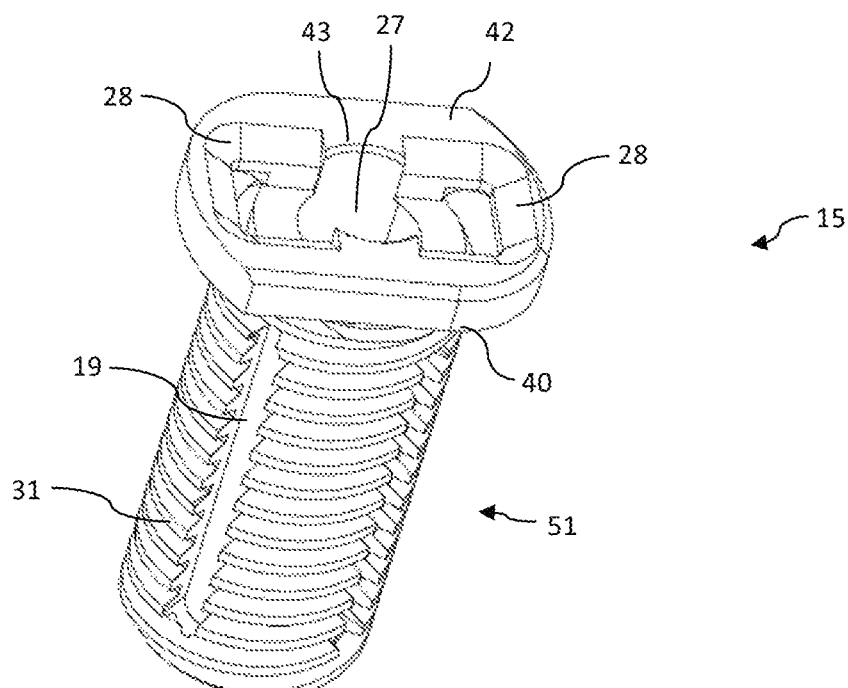
FIG. 9 is a perspective view of the inner tubular core forming part of the implant assembly of FIG. 1.
Figure 10:
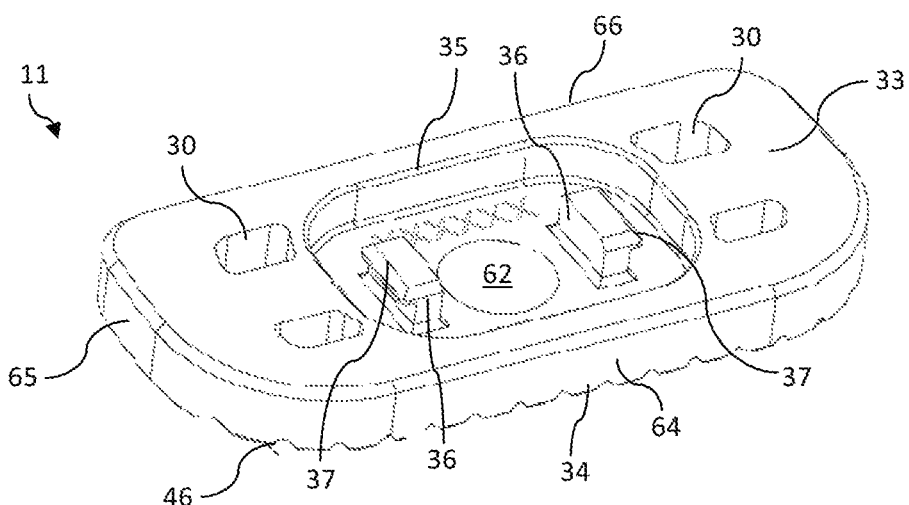
FIG. 10 is a top perspective view of one example of an endplate forming part of the implant assembly of FIG. 1.
Figure 11:
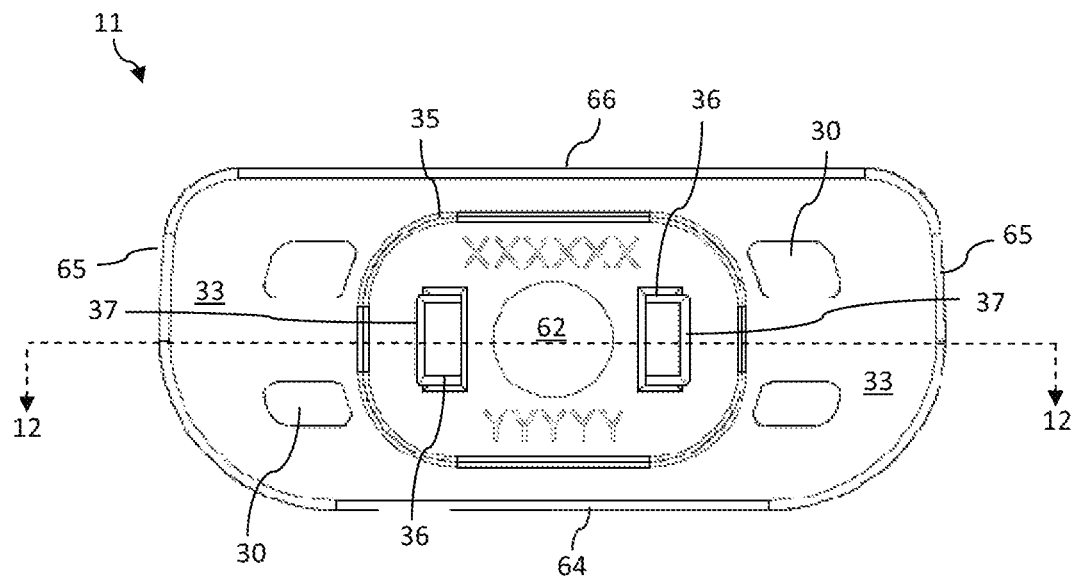
FIG. 11 is a top view of the endplate of FIG. 11.

The inner tubular core 15, illustrated in FIG. 9, is composed of a first end 40 and a generally elongated tubular body 51 extending centrally from the first end 40, and with at least one generally helical exterior thread 31. The first end 40 of the inner tubular core 15 includes endplate attachment feature 42, as will be discussed in greater detail below. One or more guide tracks 19 ingrained into the exterior wall of the tubular body 51 run parallel to the central axis of the tubular body 51. The guide track 19 receives guide pins 20 which extend through the outer tubular core 14. A guide pin 20 travels along a guide track 19, rotationally fixing inner tubular core 15 to outer tubular core 14, while permitting longitudinal movement therebetween. A guide pin 20 may have threaded features that allow it to screw into threaded holes in the wall of the outer tubular core. The threads of the guide pins 20 may be surface treated (e.g. bead blasted) to cause the surface of the threads to be roughened, which can assist in preventing slippage or back-out of the guide pins 20. The rotational fixation between the inner tubular core 15 to outer tubular core 14 ensure that the inner tubular core 14 and outer tubular core 14 (and the vertebrae engaging endplates 11) remain in the desired orientation as the vertebral body implant assembly 10 is adjusted, and for the duration that it is implanted in a patient. A central lumen 27 through the inner tubular core 15 enables additional bone growth promoting material to be placed within the core expanding body 12, and ultimately to allow new bone to form uninterrupted through the entire central axis of the vertebral body implant assembly 10. The central lumen 27 may be generally cylindrical in shape (having a generally circular cross-section) or in the alternative may have a cross section having any geometric shape without departing from the scope of the present invention.

According to one example embodiment, the vertebral body implant 10 the core can be made to the following dimensions. The inner and outer diameter of the tubular body 51 may be generally in the range of 6.1 to 13.1 mm and 12.2 to 16.7 mm, respectively. The height of the inner tubular core 15 may be generally in the range of 19.4 to 38.9 mm. The inner and outer diameter of the adjustment ring 13 may be generally in the range of 10.4 to 15.7 mm and 18.0 to 22.0 mm, respectively. The height of the adjustment ring 13 may be generally 7.6 mm. The inner and outer diameter of the outer tubular core 14 may be generally in the range of 11.9 to 16.5 mm and 18.0 to 22.0 mm, respectively. The height of the outer tubular core 14 may be generally in the range of 14.8 to 34.3 mm.

FIGS. 10-12C illustrate in greater detail the features that allow the attachment of the endplates 11 to the expanding tubular core 12. The endplate 11 includes a first surface 33, a second surface 34, a recessed tubular core attachment feature 35, and at least one window 30 through the endplate 11. The windows 30 allow bone growth to form through the endplate 11. The first surface 33 is generally flat, except for the recessed tubular core attachment feature 35. Moreover, although the perimeter of the recessed tubular core attachment feature 35 is shown as rectangular in shape with rounded corners, it will be appreciated that the perimeter shape may be provided in any number of suitable shapes or dimensions without departing from the scope of the invention, provided that the perimeter shape allows the endplate attachment features 42, 22 to be received therein. The tubular core attachment feature 35 includes at least one center hole 62 and at least one toothed flange 36 with a distal step feature 37. The toothed flanges 36 are generally the height of the recess of the tubular core attachment feature 35 and their distal step feature 37 extends out from the toothed flange 36 in the lateral direction.

The endplate attachment feature 42 of the inner tubular core 15 is partially responsible for the secure attachment of an endplate 11 to the first end 40 of the inner tubular core 15. The endplate attachment feature 42 includes tapered transitions 28 into the central opening 43, and an attachment under-step 29. The central opening 43 allows the continuous formation of new bone growth throughout the entire length of the inner tubular core 15. The tapered transitions 28 act as guides for toothed flanges 36 of the endplate 11. As the toothed flanges 36 engage the tapered transitions 28, the toothed flanges 36 are deflected inward. After the toothed flanges 36 travel the length of a tapered transition 28, the toothed flanges 36 return back to their natural positions and engage the attachment under-step 29 (and best viewed in FIG. 12B), locking the endplate 11 to the core expanding body 12.

The perimeter shape of the endplate attachment feature 42 of the inner tubular core 15 may be provided in any number of suitable shapes or dimensions without departing from the scope of the invention, provided that the perimeter shape corresponds to the perimeter shape of the tubular core attachment feature 35 and allows the tubular core attachment feature 35 to be received therein.

Figure 12A:
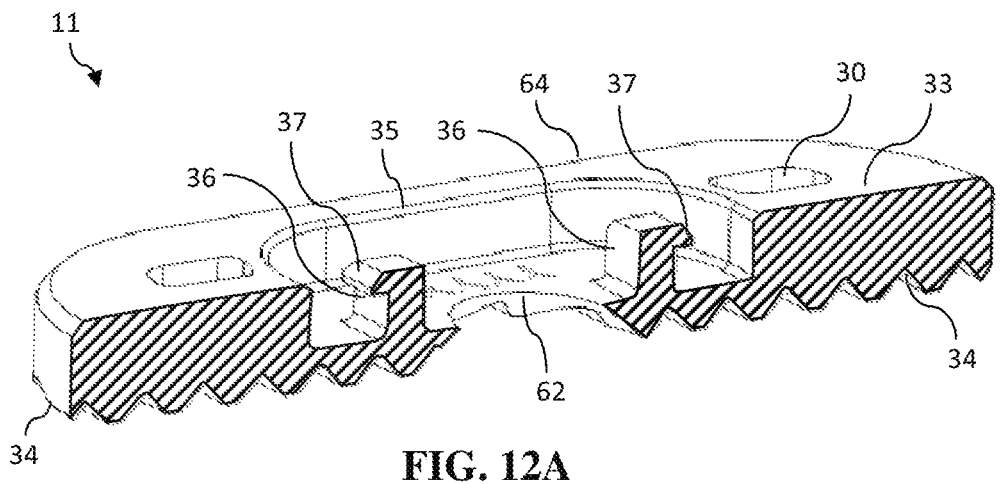
FIG. 12A is a cross section view of the endplate of FIG. 11 taken along line 12-12 of FIG. 11.
Figure 12B:
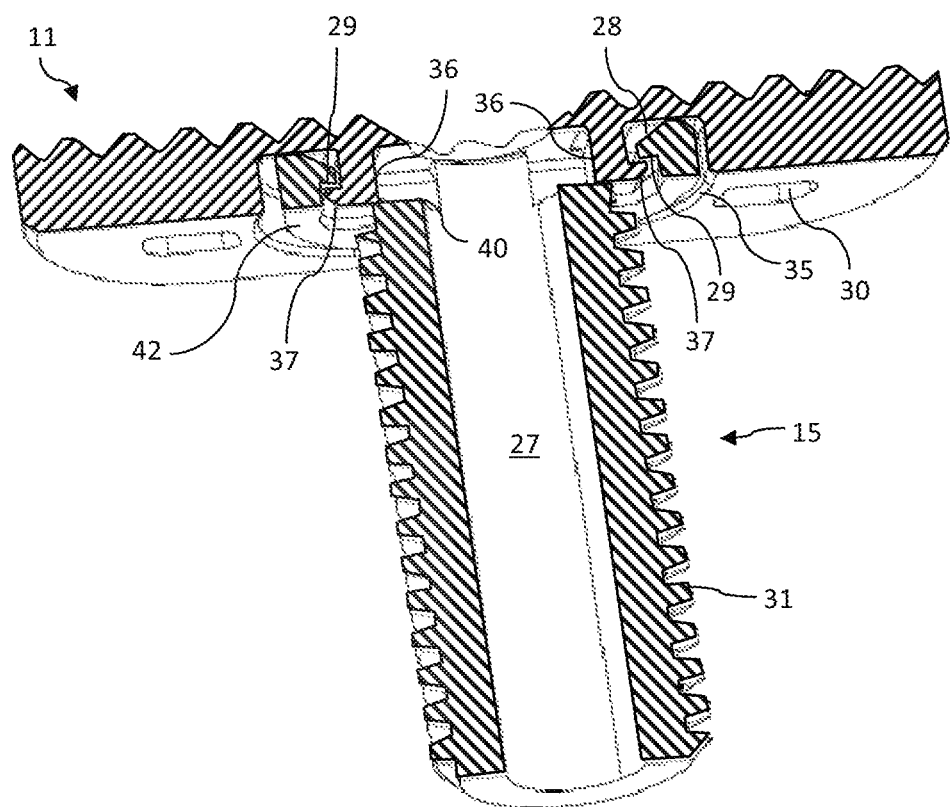
FIG. 12B is a cross section view of the endplate and inner tubular core of the implant assembly of FIG. 1.
Figure 12C:
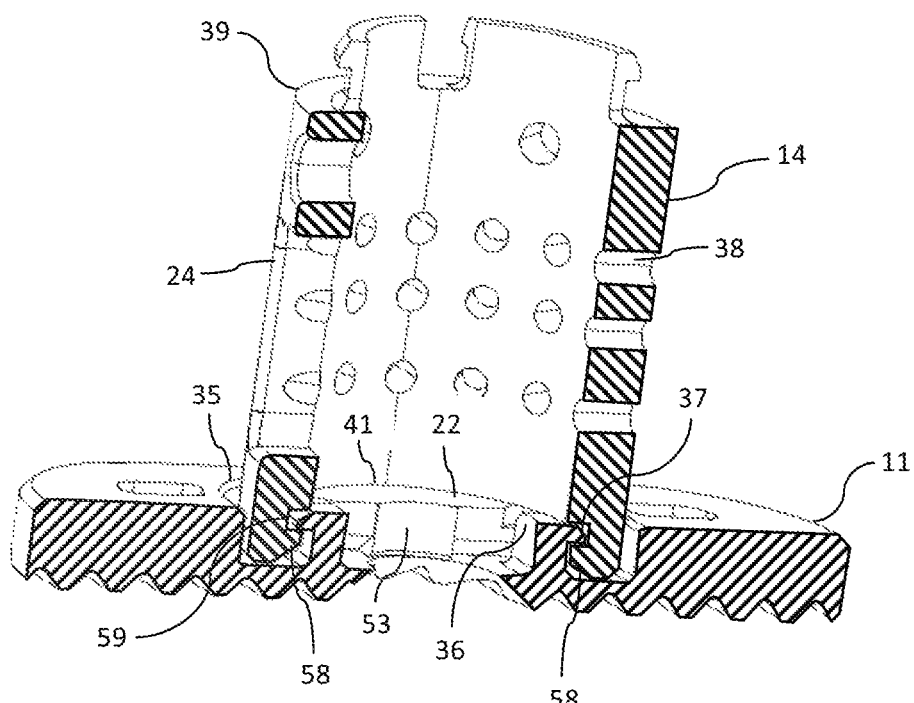
FIG. 12C is a cross section view of the endplate and outer tubular core of the implant assembly of FIG. 1.

FIG. 12C illustrates the attachment of an endplate 11 to the endplate attachment feature 22 of the outer tubular core 14. The endplate attachment feature 22 is partially responsible for the secure attachment of an endplate 11. The endplate attachment feature 22 includes tapered transitions 58 into the central opening 53, and an attachment under-step 59. The corresponding features and functions are substantially identical to those of the endplate attachment feature 42 described previously, such that a repeat discussion is not necessary.

The endplate attachment features 42, 22 allow for the unique ability to customize the tubular core expanding body 12 with various endplate 11 configurations. The ability to customize the core expanding body 12 may provide numerous advantages. By way of example, the customizable core expanding body 12 can be used in a variety of surgical approaches (e.g. anterior, anterior-lateral, lateral, etc.). By way of further example, the customizable core expanding body 12 can be placed in a variety of positions along the spine, and the customizable core expanding body 12 can be made compatible with a variety of conditions of the surrounding vertebral bodies (e.g. partial removal of vertebral body).

The vertebral body implant assembly 10 is preferably composed of either metal (e.g. titanium, stainless steel, etc.) or polymer (e.g. poly-ether-ether-ketone (PEEK)). When the implant assembly is made out of a polymer, one or more marker rods 46 are preferably composed of a radiopaque material (e.g. titanium) and are positioned within the vertebral body implant assembly 10 so that the positioning of the vertebral body implant assembly 10 can be visible upon X-ray imaging. This visual indication may be obtained either post-operatively or intra-operatively to confirm placement of the vertebral body implant assembly 10. Additionally, in patients where one or more vertebral bodies have been removed due to diseases, such as tumors, and an vertebral body implant assembly 10 has been implanted between the remaining vertebral bodies, it is beneficial during post-operative x-ray imaging to be able to see through the implant in order to detect any reoccurrence of the disease.

Figure 13:
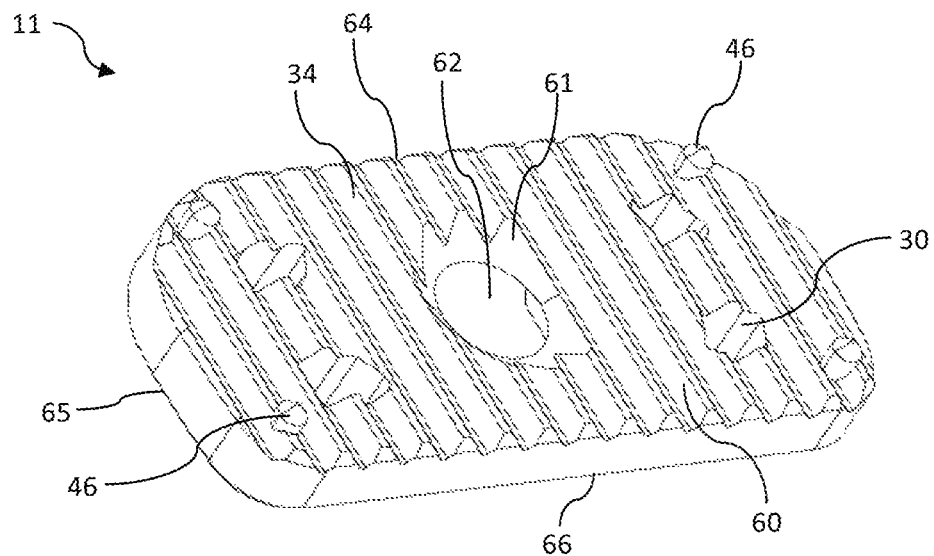
FIG. 13 is a bottom perspective view of the endplate of FIG. 10.

FIG. 13 illustrates the second surface 34 of the endplate 11 which includes one or more liner ridges 60, a taper 61 around the center hole 62, an anterior side 64, a posterior side 66, lateral sides 65, and one or more marker rods 46. When implanted, the second surface 34 is configured to be positioned against the adjacent vertebral body with the anterior side 64 positioned generally towards the anterior side of the adjacent vertebral body. The generally larger radii corners at the ends of the anterior side 64 are configured to generally conform to the natural shape of the anterior portion of a vertebral body. Endplate 11 is configured for a preferred use through a lateral approach to the spine, and preferably when endplate coverage is desired to span across the ring apophysis of the vertebra. The distance between the two lateral sides 65 has a length dimensioned to extend generally across the space from the apophyseal ring at one lateral aspect of the spine to the apophyseal ring at the other lateral aspect of the spine. This allows the endplate 11 to provide more support and distribute the weight more evenly throughout the adjacent vertebral body, which lessens stress and potential damage to the adjacent vertebral body. The ridges 60 provide additional placement stabilization and are shown in this embodiment to be generally parallel to the lateral sides 65. The ridges 60 may also travel parallel to or in angled directions from the anterior or posterior side 64, 66, without departing from the scope of the invention. While the ridges 60 are shown as linear, it will be appreciated that the ridges 60 may be non-linear without departing from the scope of the present invention. The travel of the ridge 60 is generally along the entire length of the lateral side 65, but it may only travel a portion of the lateral side 65, or any side, without departing from the scope of the invention, and therefore is not limited to the length of travel that the ridge 60 makes along the second surface 34 of the endplate 11.

The tapered entry 61 from the second surface 34 into the center hole 62, works like a funnel and provides additional room to impact graft material into the center hole 62 of the endplate 11. At least one marker rod 46 is press fit into the second side 34 of the endplate 11. The formation of the marker rods 46 are shown by example to be positioned in a rectangular formation, but can be positioned in other configurations without departing from the scope of the present invention.

Figure 14:
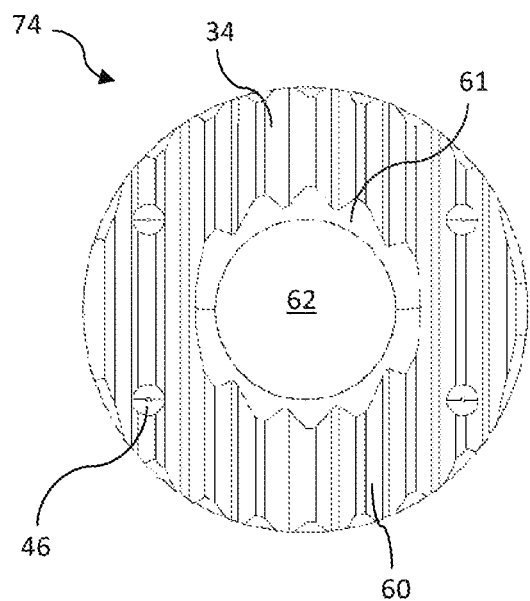
FIG. 14 is a bottom view of a second example of an endplate forming part of the implant assembly of FIG. 1.

FIG. 14 illustrates another example of an endplate 74 according to an alternative embodiment of the present invention. Endplate 74 differs from endplate 11 in the perimeter shape. The endplate 74 is generally circular in shape, and has an outer diameter dimension that is generally in the range of 22-33 mm. By way of example only, the generally circular endplate 74 is preferred for placement of a vertebral body implant assembly 10 through an anterior approach. Additionally, the generally circular shape can be beneficial in circumstances where the adjacent vertebral body is more circular in shape.

Figure 15:
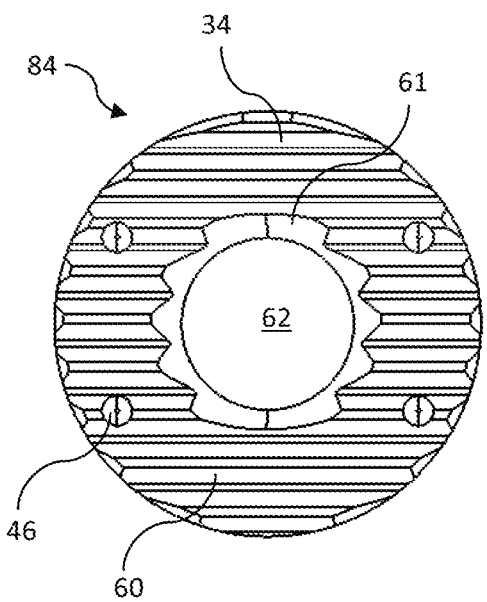
FIG. 15 is a bottom view of a third example of an endplate forming part of the implant assembly of FIG. 1.

FIG. 15 illustrates another example of an endplate 84 according to an alternative embodiment of the present invention. Endplate 84 differs from endplate 74 in the direction of their grooves relative to the generally rectangular marker rod 46 formation. The different relative directions of the grooves cater to different spinal procedures, particularly pertaining to the direction of implant insertion. By way of example only, endplate 84 is configured for a preferred use through a lateral approach to the spine.

Figure 16:
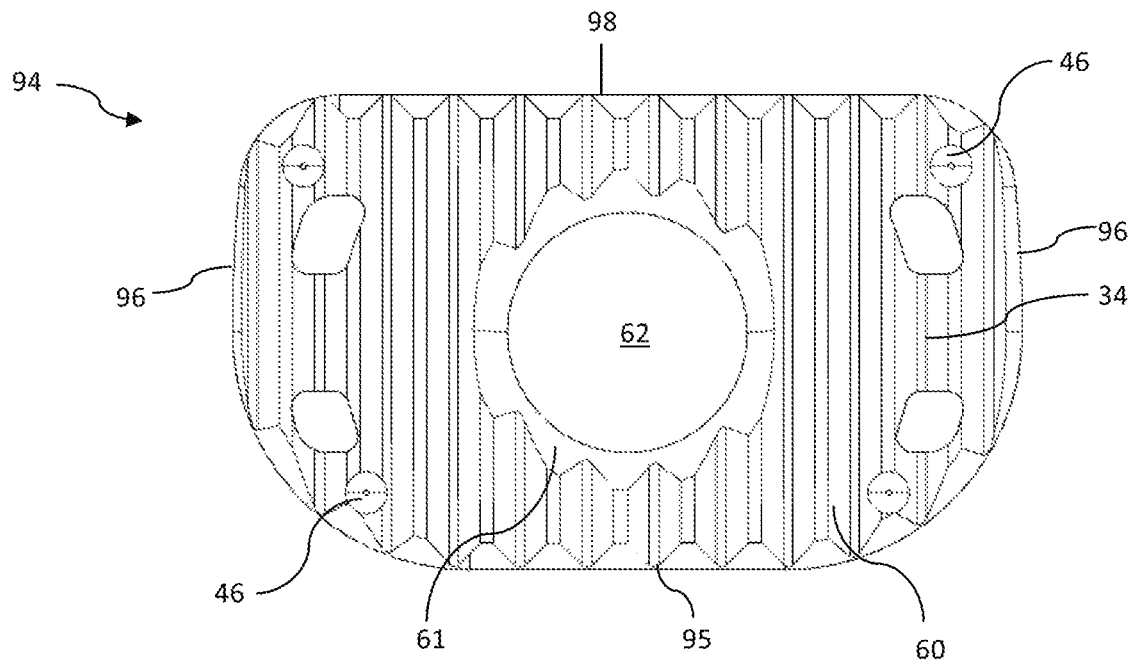
FIG. 16 is a bottom view of a fourth example of an endplate forming part of the implant assembly of FIG. 1.

FIG. 16 illustrates another example of an endplate 94 according to an alternative embodiment of the present invention. Endplate 94 is configured for a preferred use through a lateral surgical approach to the spine. Endplate 94 has generally the same outer perimeter shape as endplate 11, but in this example the anterior side 95, posterior side 98, and lateral sides 96 of endplate 94 are shown to have generally different lengths than the anterior side 64, posterior side 66, and lateral sides 65 of endplate 11. The width of an endplate is defined as the distance between the anterior side and posterior side of an endplate. Therefore, the width of endplate 11 and endplate 94 is preferably dimensioned generally in the range of 18-22 mm. The length of an endplate is defined as the distance between the opposing lateral sides of an endplate. Therefore, the length of endplate 11 and endplate 94 is preferably dimensioned generally in the range of 30-60 mm. The variable lengths of the sides of endplate 94 and endplate 11 make the core expanding body 12 even more customizable and enable the vertebral body implant assembly 10 to maximize the surface area contact between the endplates 11, 94 and the adjacent vertebral body, resulting in the ability to provide the most stable support.

Figure 17:
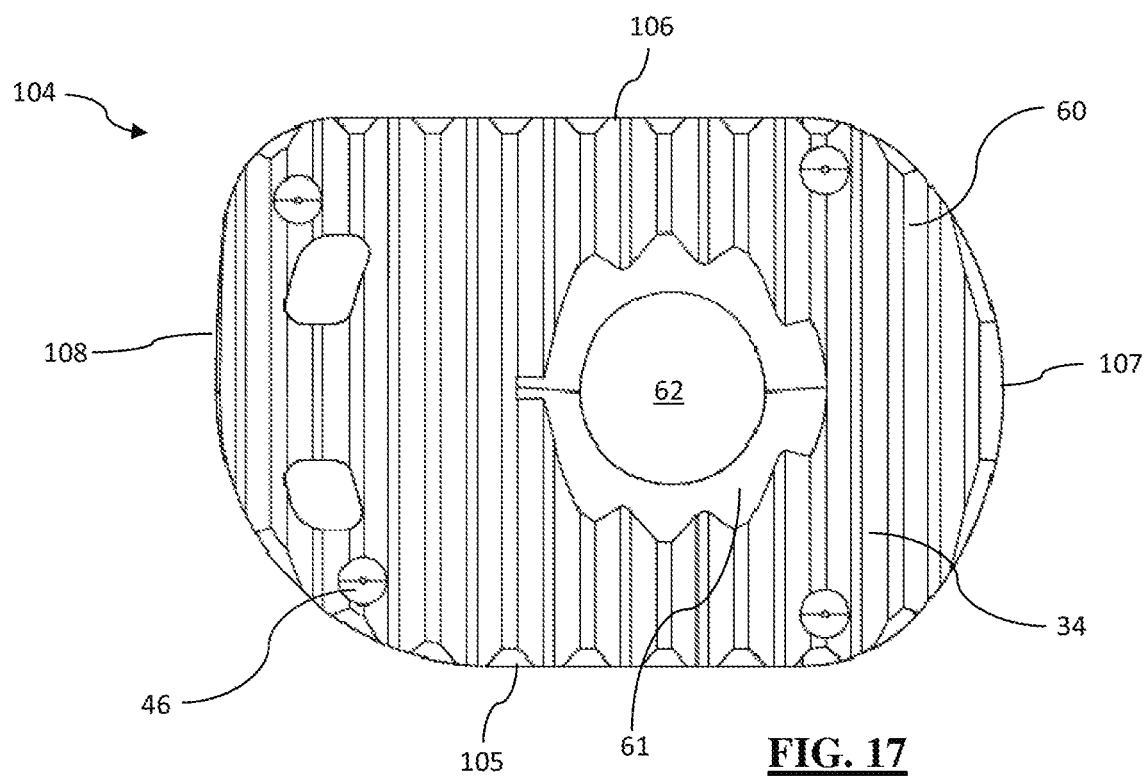
FIG. 17 is a bottom view of a fifth example of an endplate forming part of the implant assembly of FIG. 1.

FIG. 17 illustrates another example of an endplate 104 according to an alternative embodiment of the present invention. The asymmetrical shape of endplate 104 is configured for a preferred use through a lateral approach, and generally under the circumstance where a partial removal of the adjacent vertebral body has been performed and endplate coverage is to be biased in one direction relative to the core expanding body 12. Endplate 104 includes an anterior side 105, a posterior side 106, a rounded lateral side 107, and a second lateral side 108. The width of endplate 104 is preferably dimensioned generally in the range of 18-22 mm. The length of endplate 104 is preferably dimensioned generally in the range of 27-40 mm.

Figure 18:
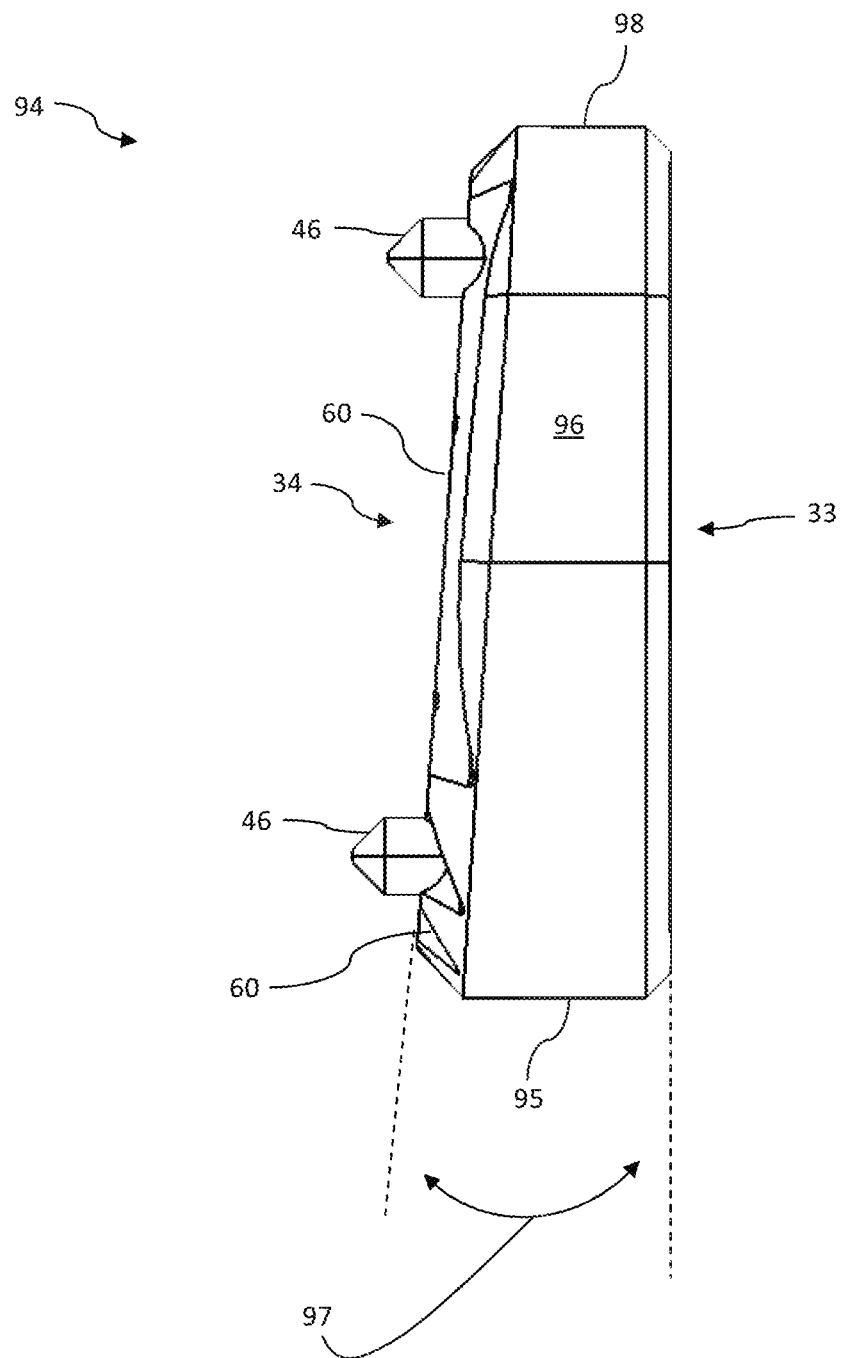
FIG. 18 is a side view of the endplate of FIG. 16.

FIG. 18 illustrates an example of the angle 97 formed between the first surface 33 and second surface 34 of endplate 94. The angle 97 that will be described for endplate 94 is available in any of the previously described endplates and is therefore not limited to only endplate 94. By way of example only, the angle 97 of the endplate 94 is preferably dimensioned generally in the range of 0-15 degrees and functions to improve the natural curvature of the spine when implanted. The preferred direction of the angle 97 formed between the first surface 33 and second surface 34 lies generally in a plane that is either along or parallel to a ridge 60, which in this example also happens to be parallel to the lateral sides 96. This configuration is intended to accompany specific procedures and directions that the endplate 94 will be implanted relative to adjacent vertebral bodies. Additionally, the angle 97 that is formed between the first surface 33 and second surface 34 may benefit the maintenance or correction of, for example, either the lordotic or kyphotic curvature of the spine, depending on the direction of angulation. By way of example only, if the distance between the first surface 33 and second surface 34 is greater at the anterior side 95 than the posterior side 98 of the endplate 94, then it can be assumed that the endplate 94 is configured to have the preferred use to correct or maintain lordosis. By way of example only, the distance between the first surface 33 and second surface 34 of endplate 94 is preferably dimensioned to be generally within the range of 4.06-11.81 mm, with the 11.81 mm dimension being generally the maximum height between the first surface 33 and second surface 34 of an endplate configured with a 15 degree angle 97. In the condition where the first surface 34 and second surface 34 is in a parallel configuration (an angle 97 of zero degrees), the height between the two surfaces is preferably dimensioned to be generally 4.06 mm.

Although described with respect to specific examples of the different embodiments, any feature of the endplates disclosed herein by way of example only may be applied to any of the embodiments without departing from the scope of the present invention. Furthermore, procedures described, for example only, involving specific regions of the spine (e.g. thoracic and lumbar) may be applied to another region of the spine without departing from the scope of the present invention and dimensioning of the implant may be adjusted to accommodate any region.

Figure 19:
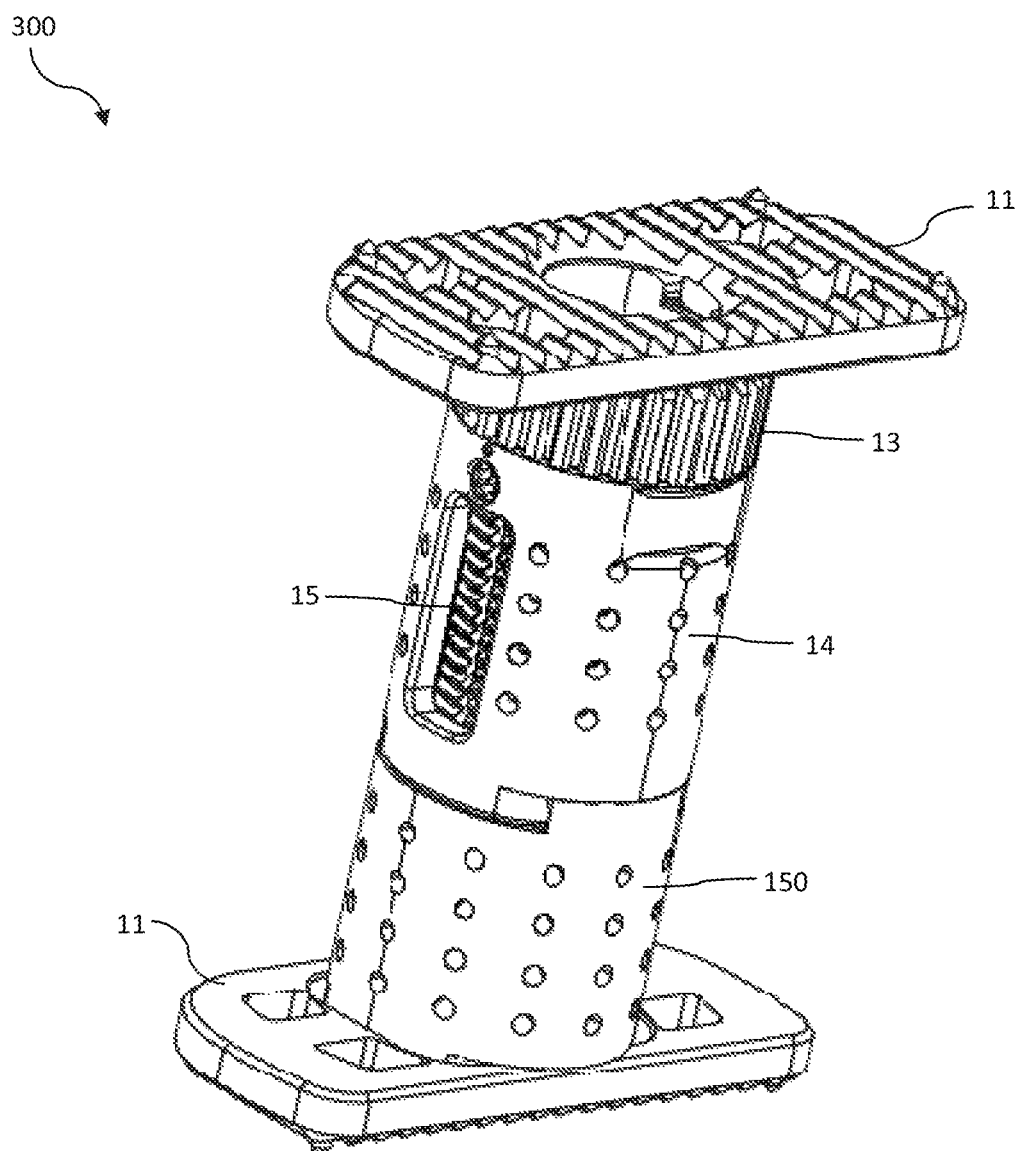
FIG. 19 is a perspective view of a vertebral body implant assembly according to another embodiment of the present invention.

FIG. 19 illustrates an example embodiment of a vertebral body implant assembly 300 including an additional extension piece 150. For simplicity, elements of vertebral body implant assembly 300 that are substantially identical to elements of vertebral body implant assembly 10 have been assigned the same callout numbers and repeat discussion of those elements is excluded. Vertebral body implant assembly 300 may be used, for example, when greater height is required to bridge the space between remaining adjacent vertebral bodies.

Figure 20:
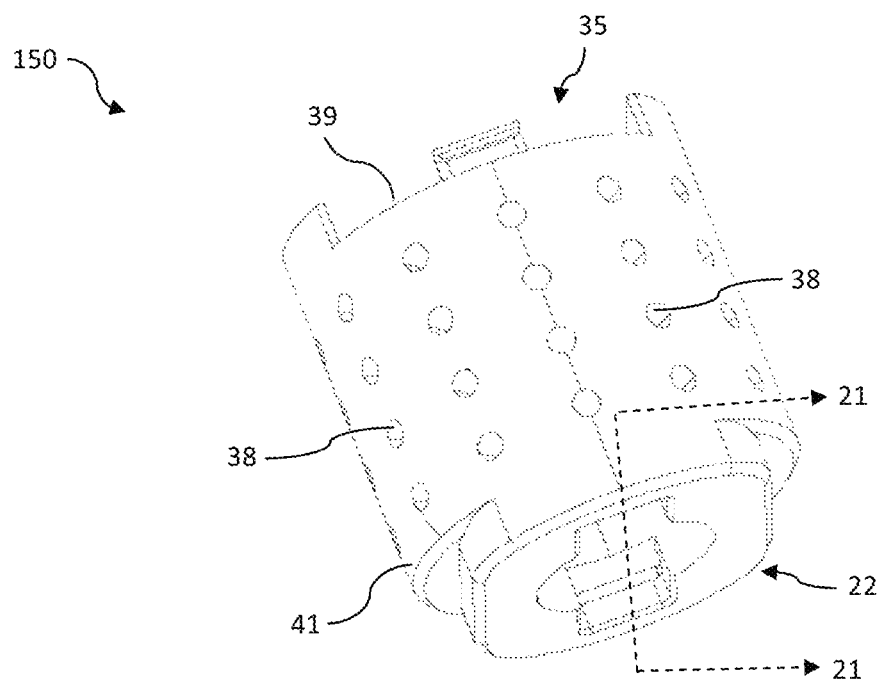
FIG. 20 is a perspective view of an extension piece forming part of the implant assembly of FIG. 22.
Figure 21:
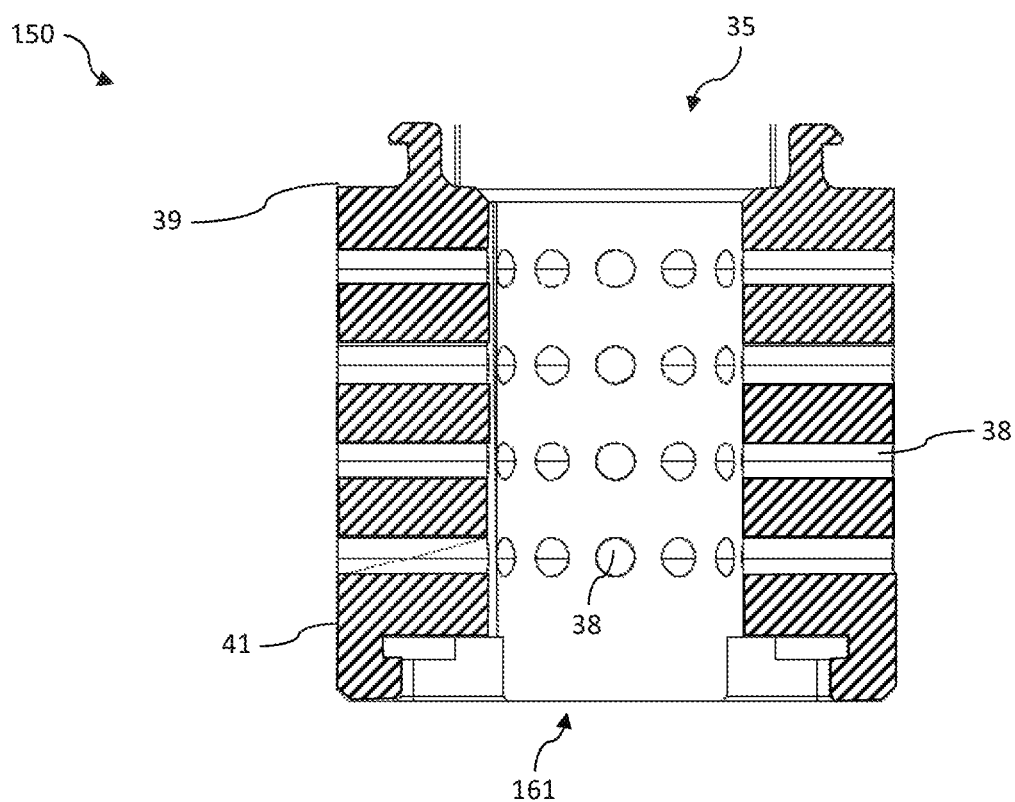
FIG. 21 is a cross section view of the extension piece of FIG. 20 taken along line 21-21 of FIG. 23.
Figure 22:
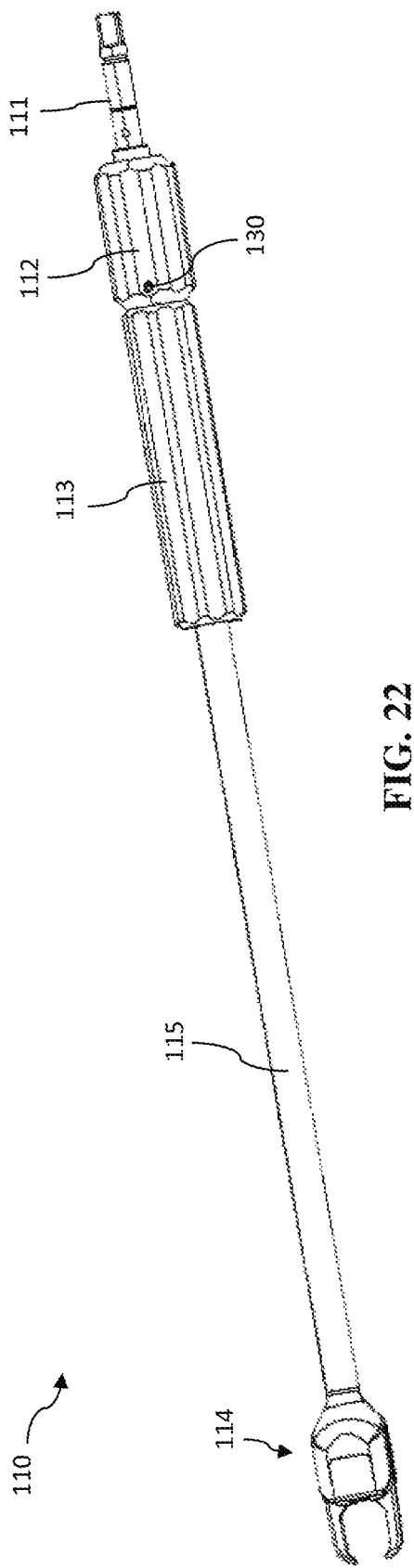
FIG. 22 is a top view of one example of a combined insertion and expansion tool, according to one embodiment of the present invention.
Figure 23:
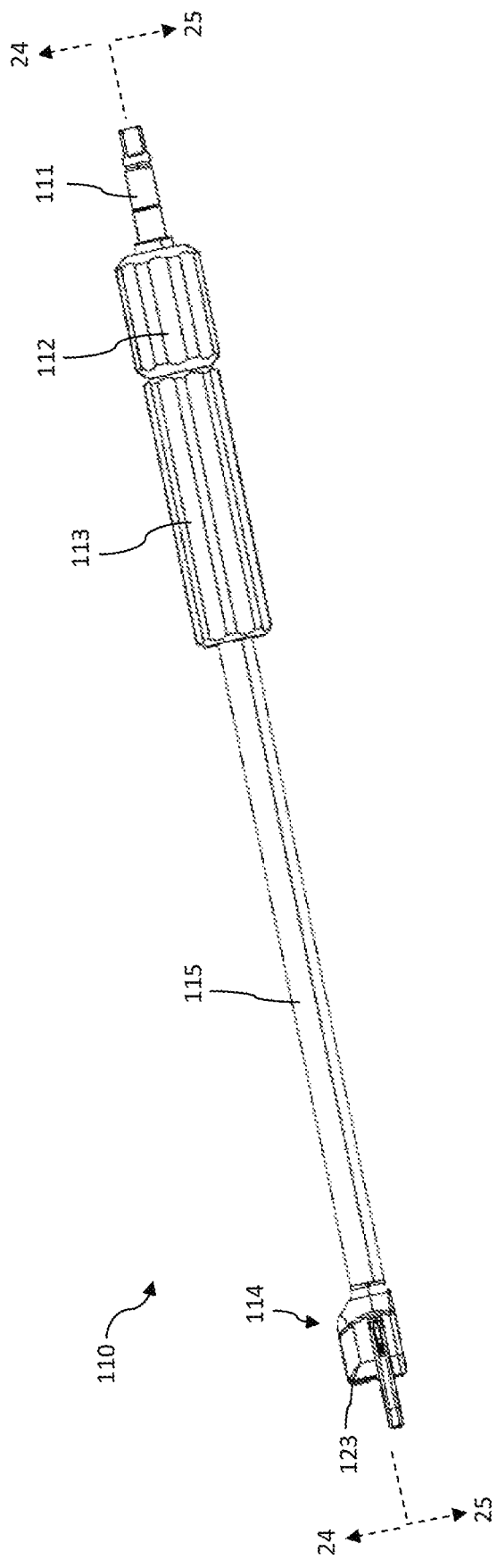
FIG. 23 is a side view of the expanding tool of FIG. 22.
Figure 24B:
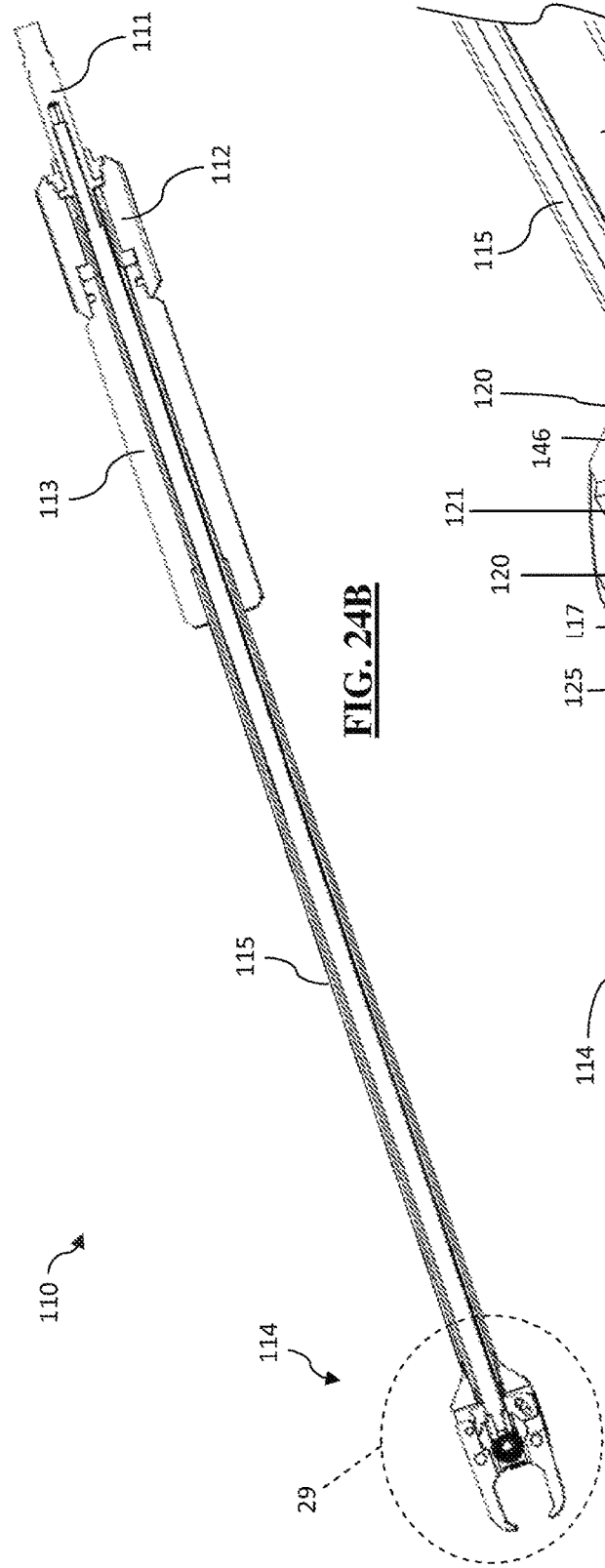
Figure 29:
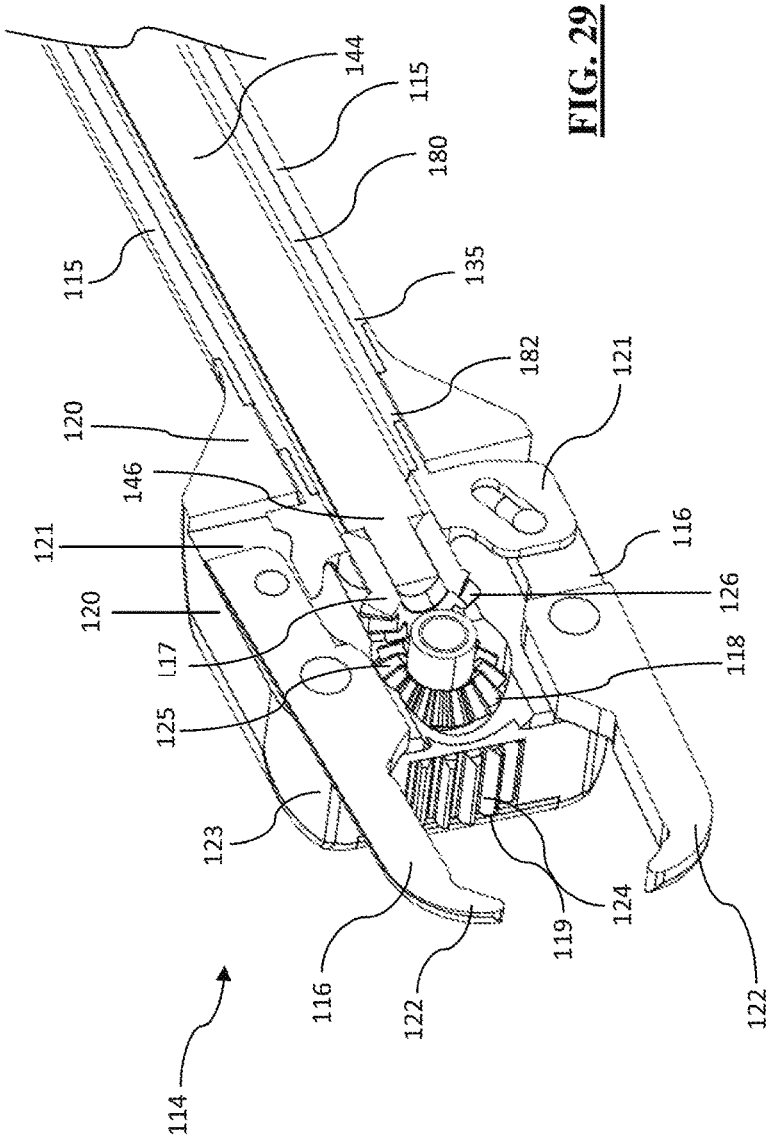
FIG. 29 is a partial view of the expanding tool taken from partial view area 29 of FIG. 24.
Figure 25:
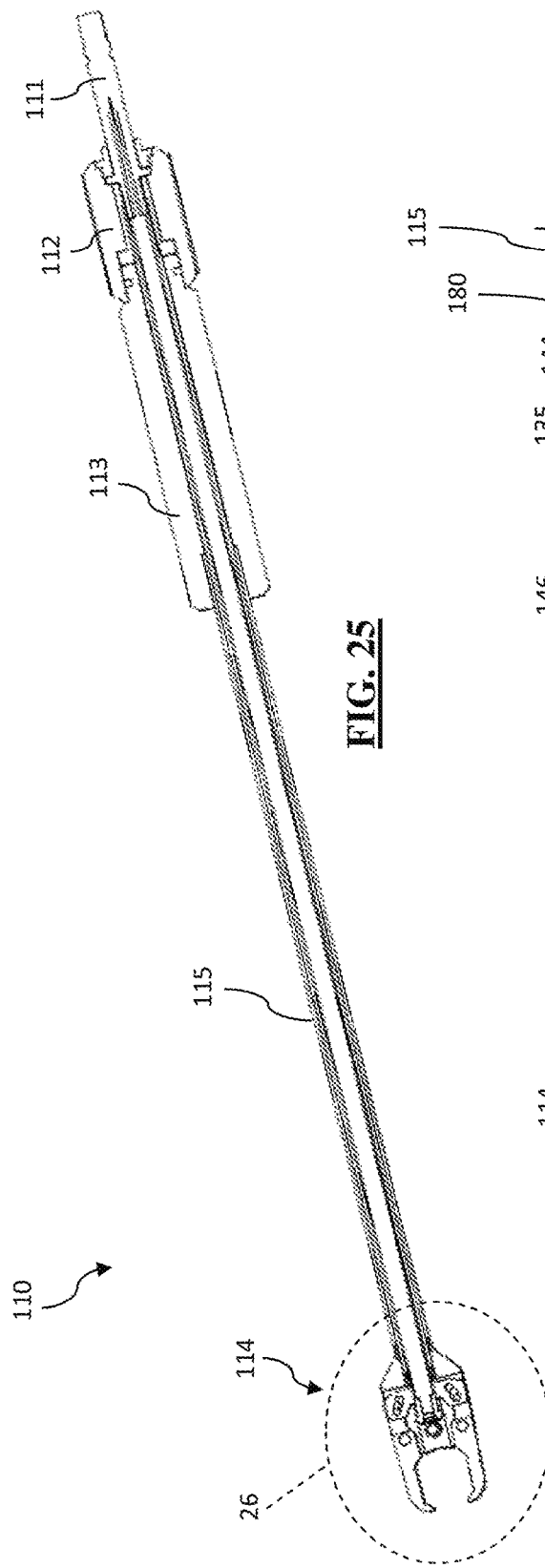
FIG. 25 is a cross section view of the expanding tool of FIG. 23 taken along line 25-25 of FIG. 23.
Figure 26:
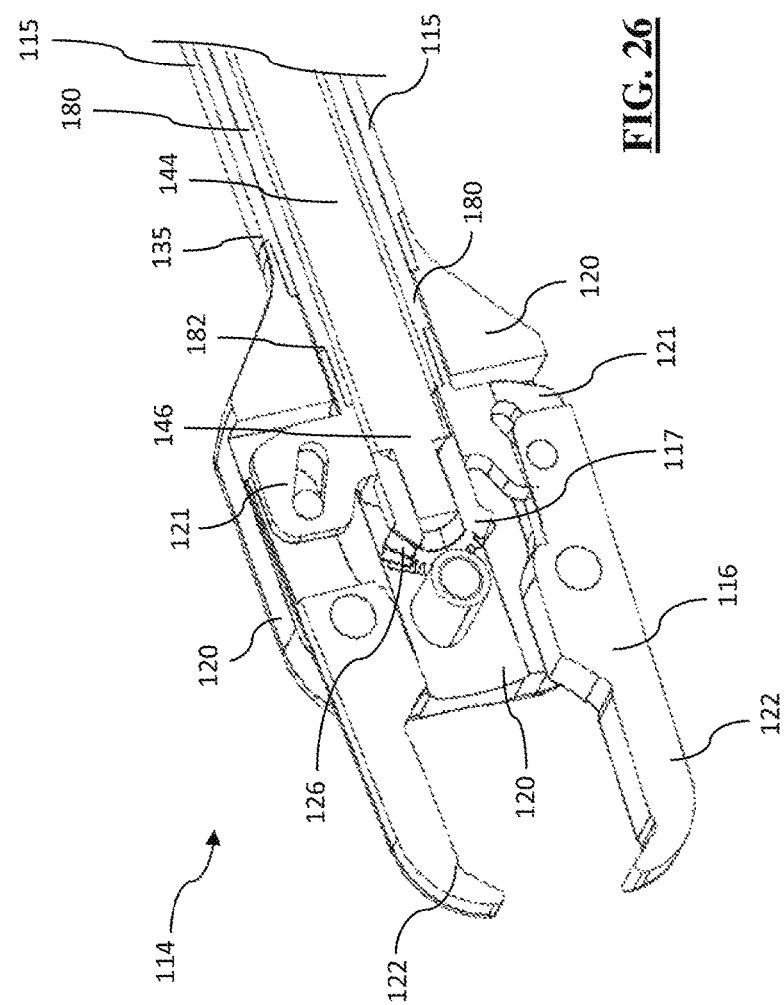
FIG. 26 is a partial view of the expanding tool taken from partial view area 26 of FIG. 25.

FIGS. 20-21 illustrate, by way of example, an extension piece 150. The features of the extension piece 150 are substantially similar to the features of the outer tubular core 14 described above, including a first end 39, a second end 41, an endplate attachment feature 22, and a plurality of holes 38. These features are substantially similar (if not identical) to the corresponding features of the outer tubular core 14, and consequently the details will not be repeated here. Centrally positioned at the first end 39 of the extension piece 150 is a tubular core attachment feature 35 which is substantially similar to the tubular core attachment feature 35 of endplate 11 described above. These features are substantially similar (if not identical) to the corresponding features of the tubular core attachment feature 35 of endplate 11, and consequently the details will not be repeated here. The inner and outer diameter of the extension piece 150 is preferably dimensioned to be generally in the range of 11.9 to 16.5 mm and 18.0 to 22.0 mm, respectively. The height of the extension piece 150 is preferably dimensioned to be generally 22.9 mm.

The extension piece 150 can be attached at either end, or both ends, of the core expanding body 12. The attachment of the extension piece 150 to either end of the core expanding body 12 is accomplished using the same feature orientations described above. For example, the tubular core attachment feature 35 of the extension piece 150 can become attached to the endplate attachment feature 22 of the outer tubular core 14 or the endplate attachment feature 42 of the inner tubular core 15. By way of example only, the extension piece 150 can be attached to the outer tubular core 14 of the core expanding body 12 by aligning them along their center axis and allowing the endplate attachment feature 22 of the outer tubular core 14 to receive the tubular core attachment feature 35 of the extension piece 150. This attachment permanently secures the anti-rotational and longitudinal fixation of the extension piece 150 to the core expanding body 12. When the extension piece 150 is attached to either end of the core expanding body 12, an endplate 11 (or any variation of endplate 11) can be attached to the extension piece 150 by aligning the endplate attachment feature 22 of the extension piece 150 with the tubular core attachment feature 35 of endplate 11 and allowing them to receive each other. This attachment permanently secures the anti-rotational and longitudinal fixation of the endplate 11 to the extension piece 150. Additionally, at least one extension piece 150 can be attached to at least one extension piece 150 in order to accomplish additional height of the vertebral body implant assembly 10. An extension piece 150 can be attached to another extension piece 150 by aligning a tubular core attachment feature 35 of one extension piece 150 with an endplate attachment feature 22 of a second extension piece 150 and allowing the attachment features 35, 22 to receive each other. The attachment between a tubular core attachment feature 35 and an endplate attachment feature 22 has been previously described above, and therefore the details will not be repeated here.

FIGS. 22-31 illustrates an example of an expanding tool 110 for use with the vertebral body implant assembly 10 described above. By way of example only, expanding tool 110 includes a proximal handle 111, a medial handle 112, a distal handle 113, a distal engagement region 114, and an elongated first shaft 115. Distal engagement region 114 includes a plurality of engagement arms 116, a first gear 117, a second gear 118, a third gear 119, and a housing 120 (and best viewed in FIG. 29). By way of example only, an engagement arm 116 is composed of a base member 121 and an extension member 122 connected by a hinge. The engagement arms 116, and particularly the extension member 122, are sized and dimensioned to securely grasp the indented slots 23 of the outer tubular core 14 and secure the position and anti-rotation of the vertebral body implant assembly 10.

The opening (lateral direction) and closing (medial direction) of the engagement arms 116 can be performed by rotating the medial handle 112. The medial handle 112 is fixed to a threaded coupler 170 which has threaded features (not shown) in its inside diameter. The threaded features of the coupler 170 are engaged with the threaded features (not shown) on the outside diameter and proximal end 181 of the elongated second shaft 180. At the distal end 182 of the elongated second shaft 180, the base member 121 is attached. Therefore, when the medial handle 112 is rotated, it causes the threads of the coupler 170 to rotate (and best viewed in FIG. 28) which forces the second shaft 180 to travel linearly along its central axis and force the proximal hinge members 121 to move. By way of example only, movement of a base member 121 forces the movement of an extension member 122 in either direction (open or closed). The direction of travel of the second shaft 180 depends on the direction of rotation of the medial handle 112 and the direction of the threaded features. Therefore, by way of example only, a clockwise turn of the medial handle 112 can result in the movement of the engagement arms 116 to an open position due to the advancement of the second shaft 180 in the direction of its distal end 182. A set screw 130 (shown in FIG. 22) through the medial handle 112 engages an annular groove 131 (best viewed in FIG. 28) at the proximal end 132 of the distal handle 113 which allows the medial handle 112 to rotate freely while fixing its longitudinal position at the proximal end 132 of the distal handle 113. The distal handle 113 is permanently fixed at its distal end 133 to the proximal end 134 of the first shaft 115 which is permanently fixed at its distal end 135 to the housing 120, with both of these connections preventing longitudinal and rotational movement relative to each other. The partial function of the distal handle 113 is to provide a grasping area for the user.

The proximal handle 111 can rotate about its center axis and can do so independently from the medial handle 112, and vice versa. The end cap 165 is secured into the proximal end 140 of the medial handle 112 and one of its functions is to secure the proximal handle 111 to the proximal end 140 of the medial handle 112. Extending rigidly from approximately the center of the distal end 142 of the proximal handle 111 is the third shaft 144. At the distal end 146 of the third shaft 144 is the first gear 117 which can be caused to rotate by rotating the proximal handle 111. An adapter feature 128 at the proximal end 143 of the proximal handle 111 enables tools (e.g. t-handles, etc. —not shown) to couple to the adapter feature 128.

Figure 30:
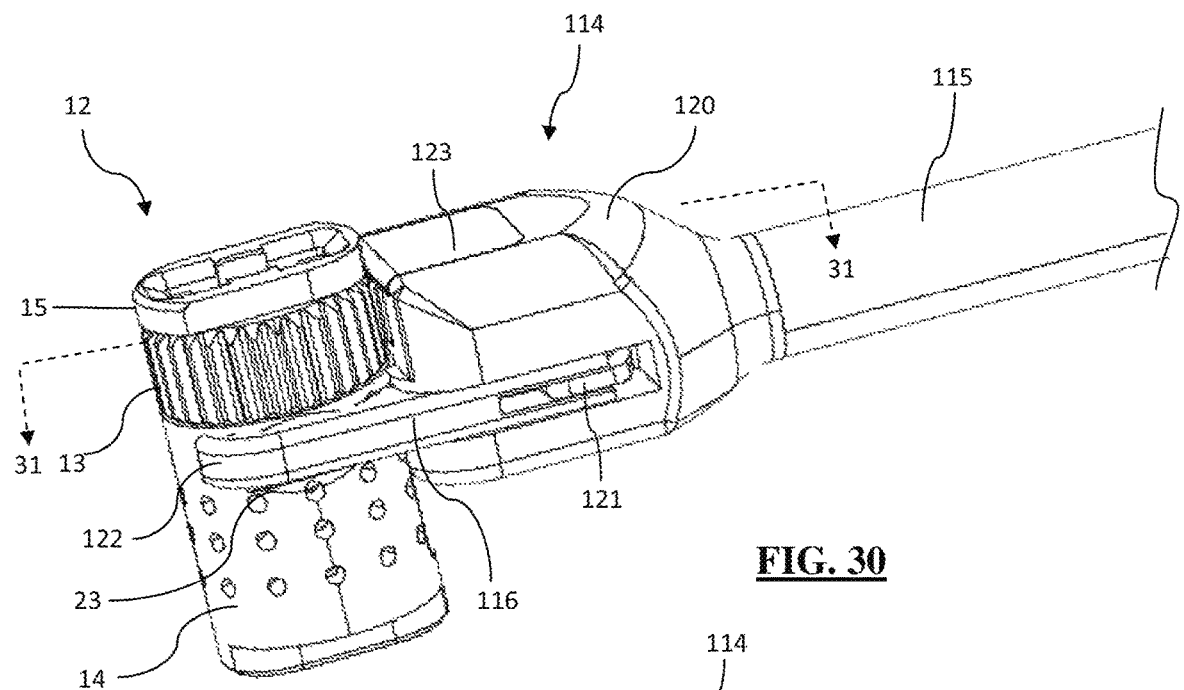
FIG. 30 is a side perspective view of the core expanding body of FIG. 7 coupled with the expanding tool of FIG. 25, according to one embodiment of the present invention.
Figure 31:
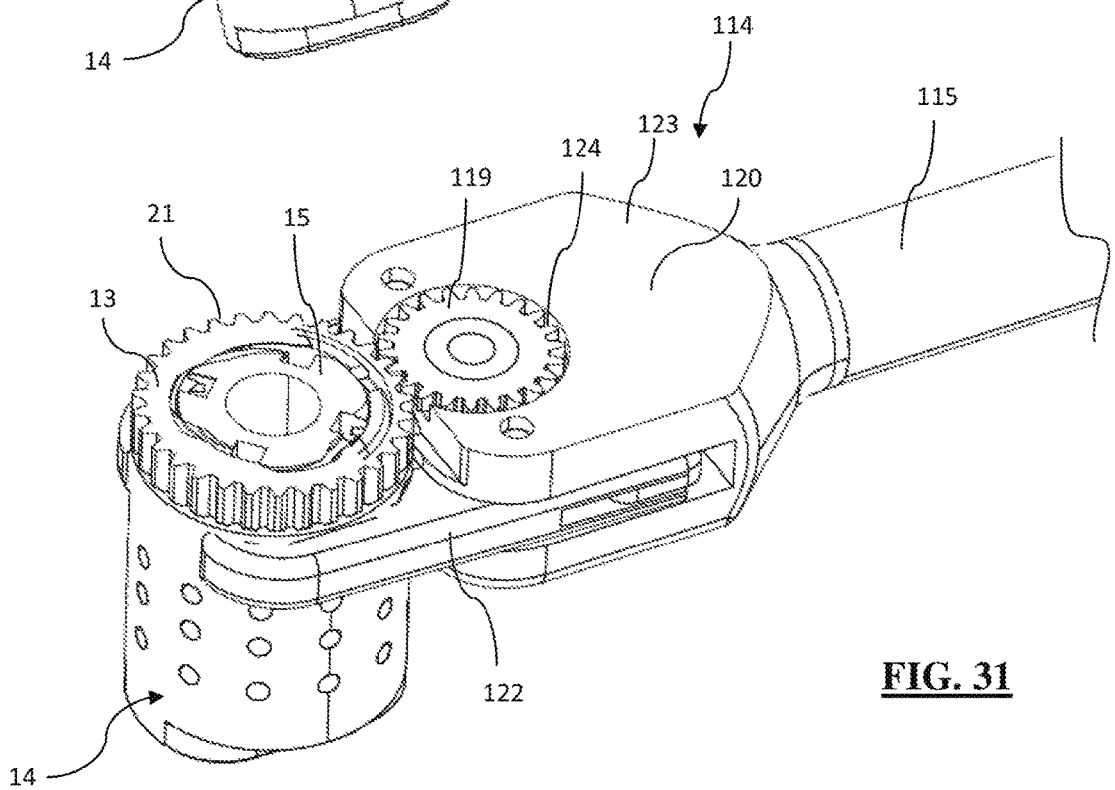
FIG. 31 is a perspective cross section view of the expanding body coupled with the expanding tool of FIG. 30 taken along line 31-31 of FIG. 30.

A third gear 119 is housed in the superior portion 123 of the housing 120 and has third gear features 124 that are compatible with the external features 21 of the adjustment ring 13 (and best viewed in FIGS. 30-31). This is so that when the expanding tool 110 is fully engaged with the vertebral body implant assembly 10, the third gear 119 is able to engage the external features 21 of the adjustment ring 13 and can cause it to rotate. The rotation of the third gear 119 is controlled by the rotation of the second gear 118 which has second gear features 125 that are compatible and engage with the third gear features 124 of the third gear 119 and cause it to rotate (and best viewed in FIG. 29). Rotation of the second gear 118 is controlled by the rotation of the first gear 117, which has first gear features 126 that are compatible and engage with the second gear features 125 of the second gear 118 and can cause it to rotate. Rotation of the first gear 117 is accomplished by rotating the proximal handle 111, as described above.

Figure 32:
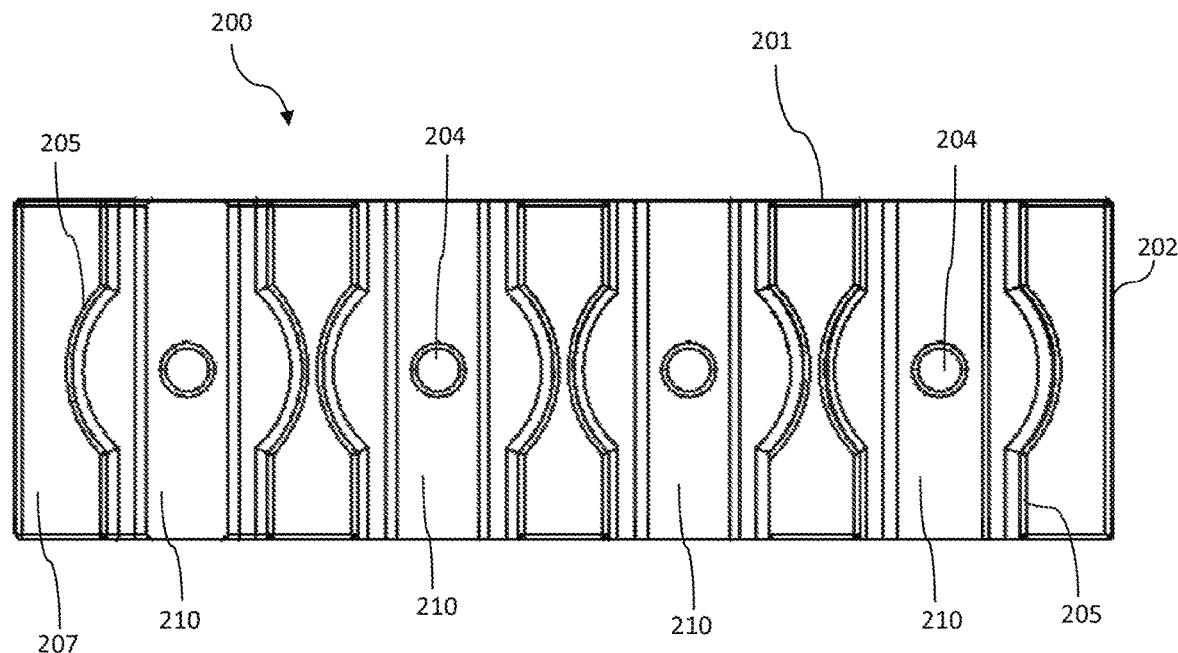
FIG. 32 is a top view of the loading block, according to one embodiment of the present invention.
Figure 33:
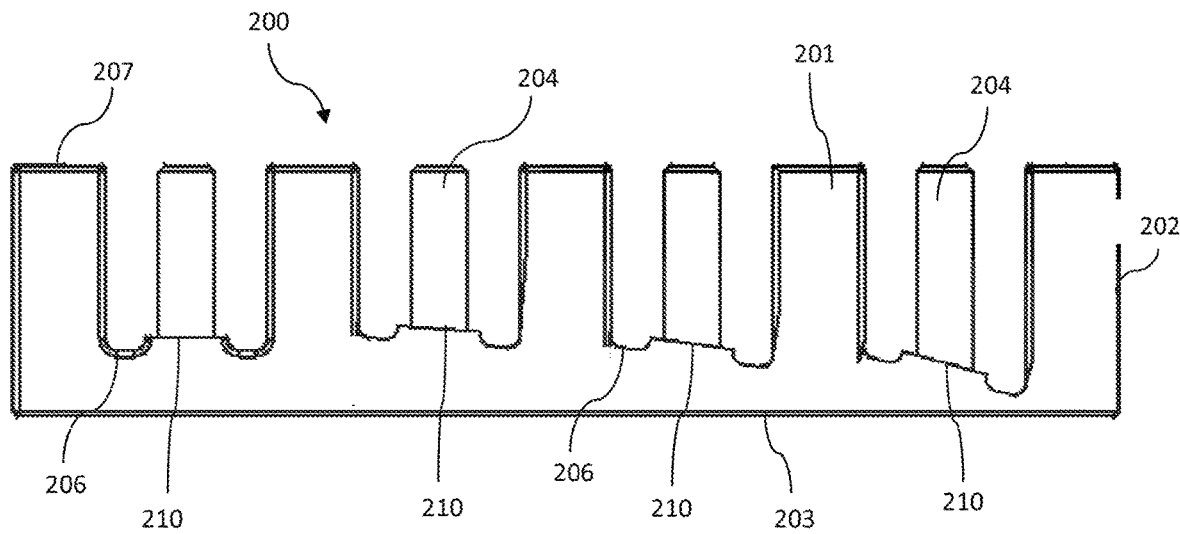
FIG. 33 is a side view of the loading block of FIG. 32.

FIGS. 32 and 33 illustrate one example of a loading block 200, which can be used for assisting in the attachment of a tubular core attachment feature 35 of an endplate to the endplate attachment feature 22, 42 of a core expanding body 12 or extension piece 150. By way of example only, loading block 200 includes a first side 201, a second side 202, a top face 207, and a bottom face 203. Additionally, loading block 200 includes endplate profile trenches 205 which consist of a center post 204, a base 210, and gutters 206. The endplate profile trenches 205, along with the center posts 204, serve as positioning guides for when the endplate is loaded, and for once the endplate is positioned in the loading block 200. By way of example, the center post, which passes through the large center hole 62 of the endplate, and the walls of the endplate profile trench 205 both provide a generally sliding fit to the center hole 62 and outer profile of the endplate being loaded into the loading block 200. Different dimensions are available for the profiles of the endplate profile trenches 205 and center posts 204 such that each available endplate previously mentioned has a center post 204 and encompassing endplate profile trench 205 that corresponds to its size and shape, and, thus, can facilitate in providing secure positioning during assembly of the endplate. Additionally, the profile shapes of the endplate profile trenches 205 are shaped to accommodate all endplate shapes, both previously mentioned (e.g. rectangular, circular) and a range of variations.

Gutters 206 in the base 210 provide, for example, additional space for any features that may extend from the base of the endplate (e.g. marker rods), allowing the second surface 34 to rest generally flush against the base 210. The base 210 of the endplate profile trenches 205 may be flat (parallel to the bottom surface 203 of the loading block 200), or may be angled so that they can accommodate endplates that have first and second surfaces 33, 34 that are angled 97 in relation to each other (for assisting in the correction or maintaining of lordosis). The angles of the bases 210 of the loading block 200 are provided in dimensions that correspond to the angles 97 of the first and second surfaces 33, 34 of the endplates (as previously discussed) for which the loading block 200 is to be used for assembly. A loading block 200 may be provided with more than one size and shape endplate profile trench 205 and center post 204 so that one loading block 200 may be used for the assembly of a variety of endplates. Additionally, more than one base 210 may have a different angle within a loading block 200.

Once an endplate is placed completely in the loading block such that the second surface 34 of the endplate is generally resting on the base 210 with its tubular core attachment feature 35 facing in the direction of the top face 207, the endplate is then ready to be assembled to an endplate attachment feature 22, 42. An endplate attachment feature 35 of either an inner or outer tubular core 14, 15, or an extension piece 150, is then inserted in the loading block 200 such that its endplate attachment feature 22, 42 is aligned with the tubular core attachment feature 35 of the endplate. Once the endplate attachment feature 22, 42 is aligned and generally resting on the tubular core attachment feature 35, a force can then be applied (for example, by using a mallet of other instrument to strike the top of the core expanding body, extension piece, or second surface 34 of the endplate that was first attached to the assembly) to cause the secure attachment of the endplate attachment feature 22, 42 to the tubular core attachment feature 35.

In an alternate embodiment, the center post 204 may include an internal thread that travels from the top surface of the center post 204 to at least a portion of its length. This internal thread could be used to allow a threaded shaft to be secured at one end to the center post 204 and still allow the endplate and mating parts to be loaded into the loading block. The opposite end of threaded shaft includes an element to attach and assist in applying the force necessary to cause the attachment of the endplate attachment feature 22, 42 to the tubular core attachment feature 35. By way of example only, this element could consist of a handle and a modified washer such that when the endplate attachment feature 22, 42 was positioned and ready to attach to a tubular core attachment feature 35, the modified washer could be placed over the opposite end of the threaded shaft and the handle could be threaded onto the opposite end of the threaded shaft. The modified washer could act as a protective barrier between the handle and the attachment piece (e.g. inner or outer tubular core) as the handle is screwed onto the threaded shaft and travels downward (toward the loading block). The handle could be screwed onto the end of the threaded shaft and continue to travel downward until it forced the modified washer against the attachment piece with enough force to cause the attachment of the endplate attachment feature 22, 42 to the tubular core attachment feature 35.

Figure 34:
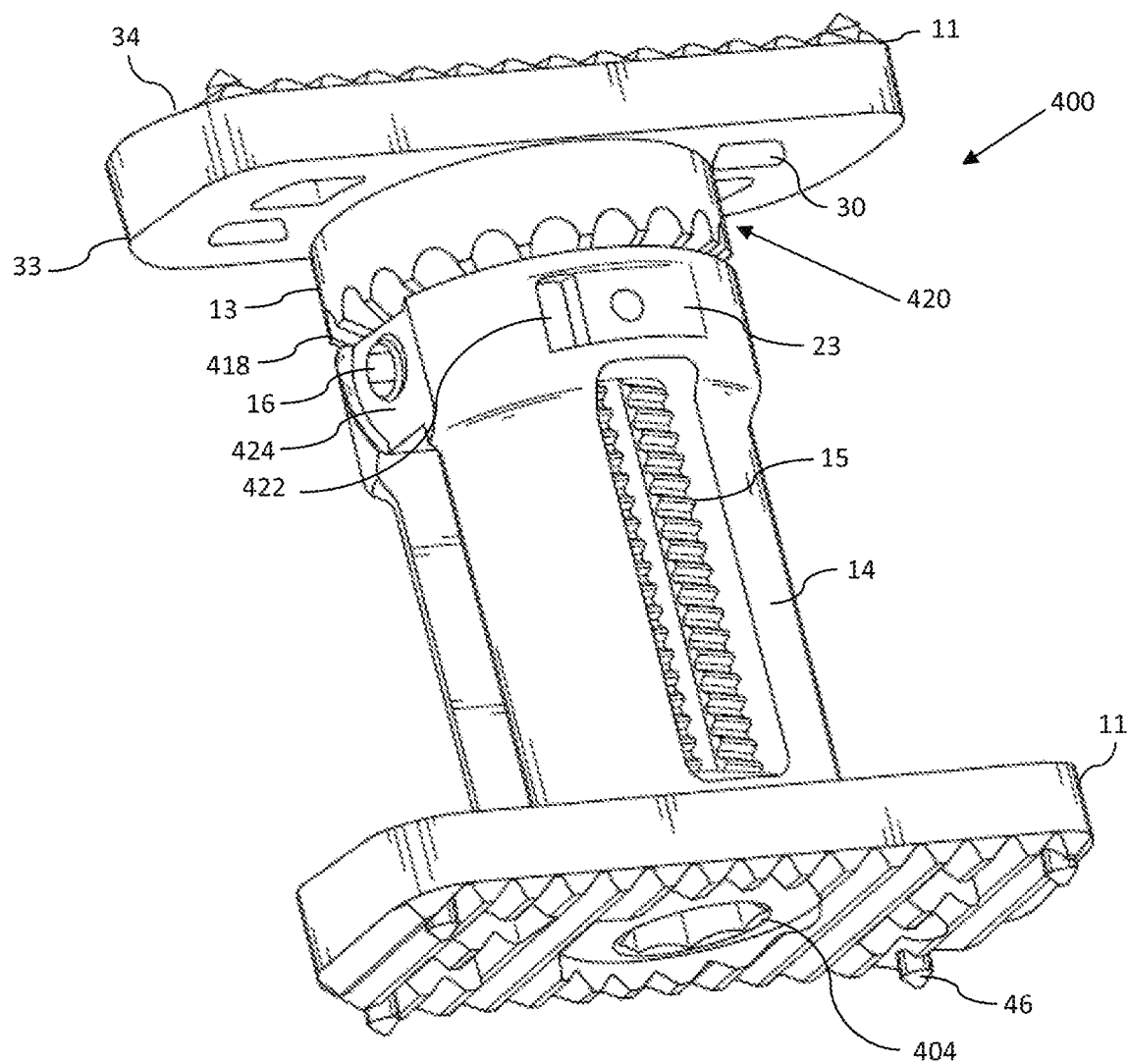
FIG. 34 is a perspective view of a vertebral body implant assembly according to another embodiment of the present invention.

FIG. 34 illustrates a vertebral body implant assembly 400 according to an additional example embodiment employing alternate mechanisms for coupling endplates 11 (or any variation described above, e.g. 74, 84, 94, 104) with the expanding core body 12, as well as for coupling the expanding core body 12 and adjustment ring 13 with an insertion/expansion tool.

Figure 35:
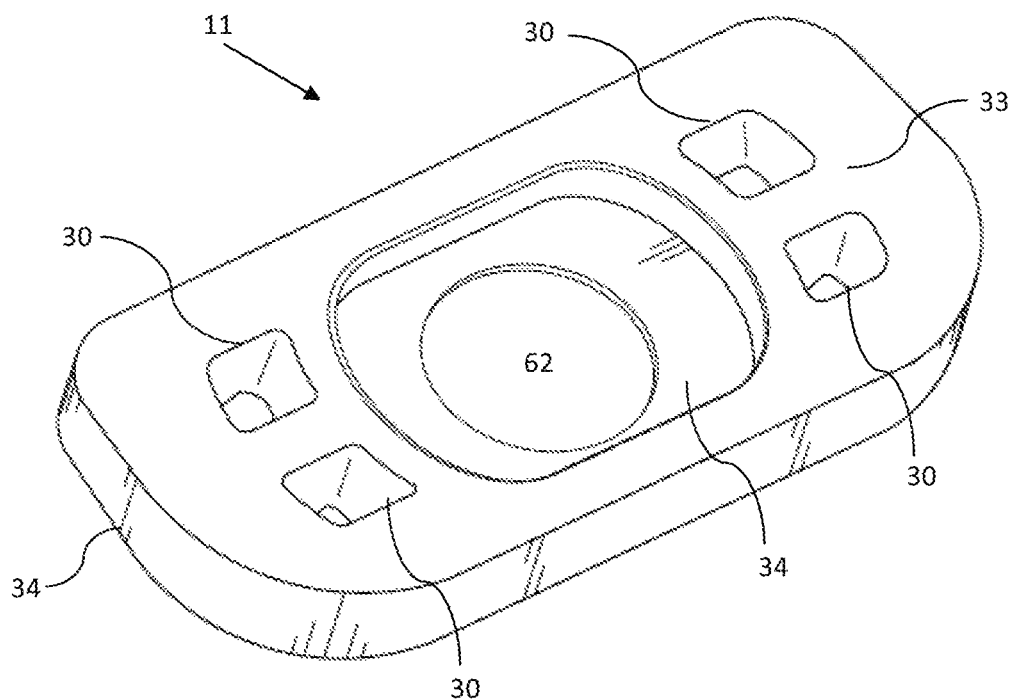
FIG. 35 is a perspective view of a first side of an endplate according to the embodiment of FIG. 34.
Figure 36:
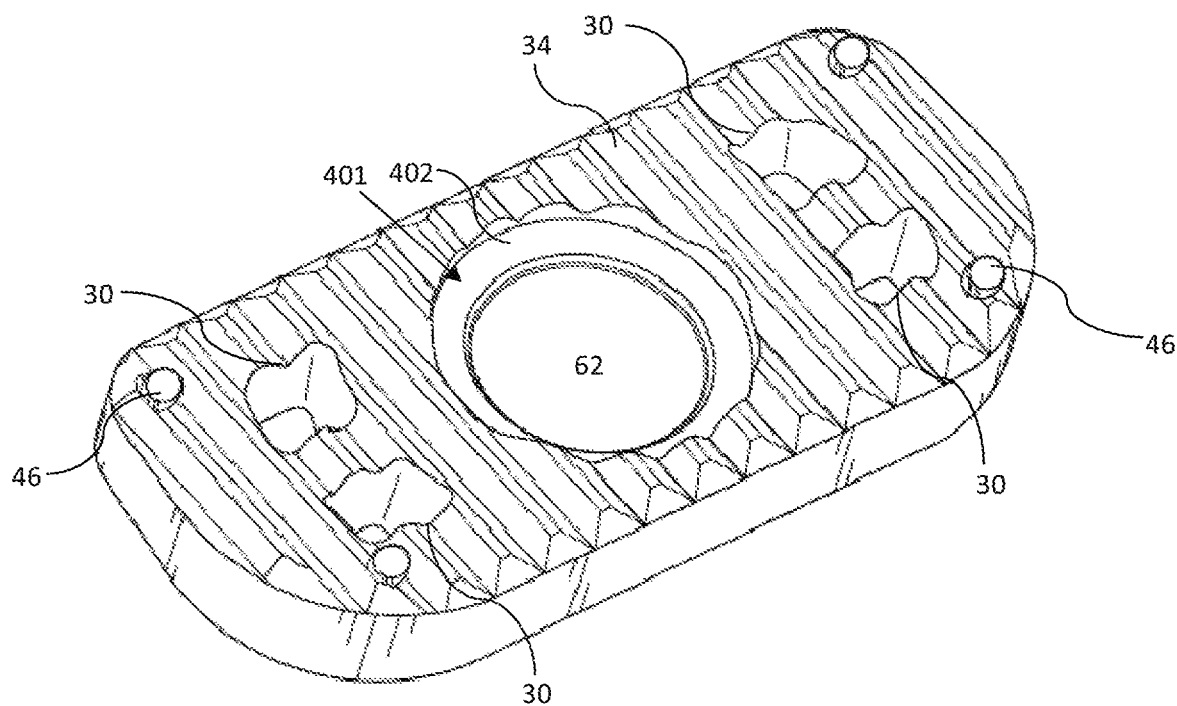
FIG. 36 is a perspective view of a second side of an endplate according to the embodiment of FIG. 34.
Figure 37:
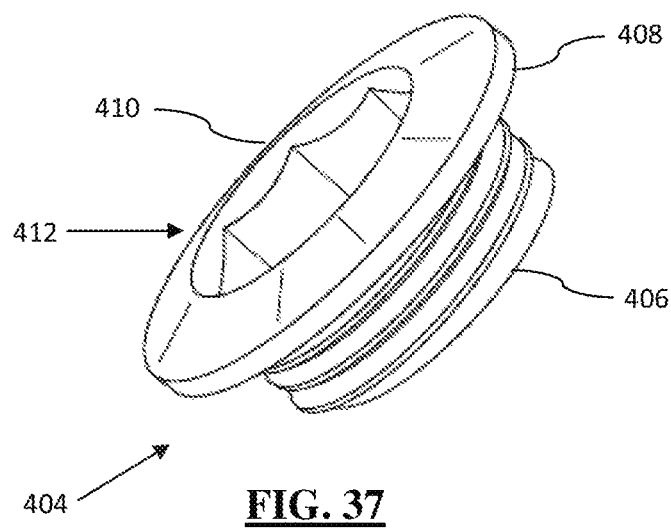
FIG. 37 is a perspective view of a lock screw for releasably fixing the endplate of FIGS. 35 and 36 to the core of the implant of FIG. 34.
Figure 38:
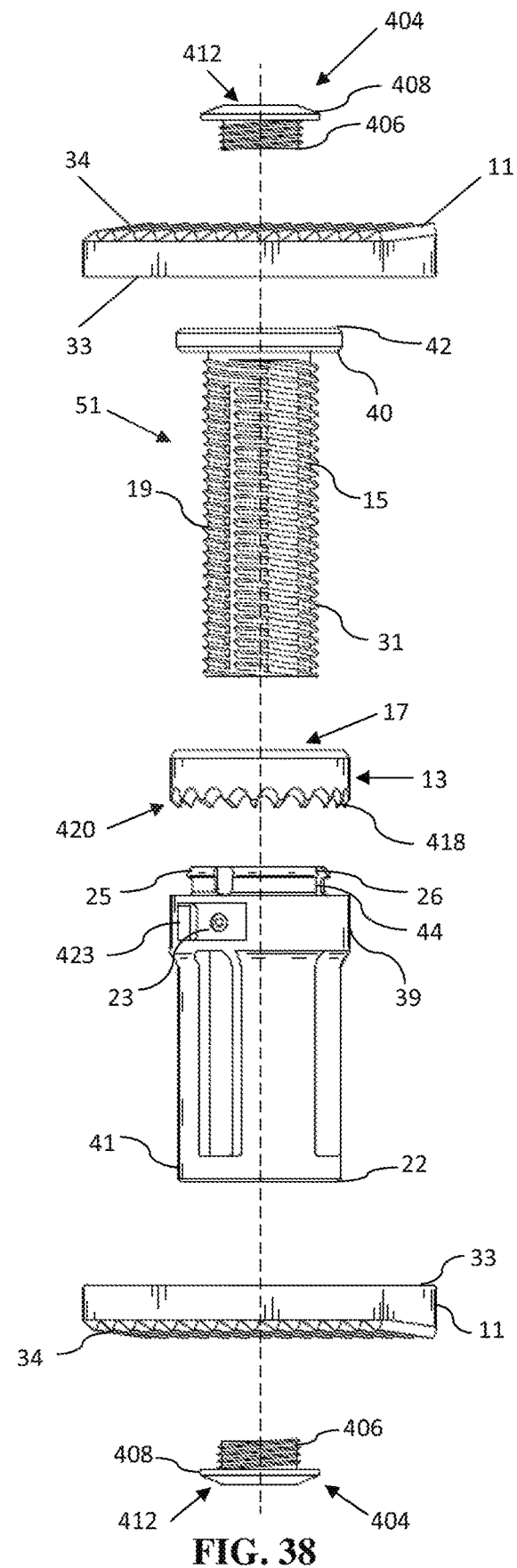
FIG. 38 is an exploded perspective view of the implant of the implant of FIG. 34.

FIGS. 35-36 illustrate, by way of example, the end plate 11. The endplate 11 includes a first surface 33, a second surface 34. The first surface 33 is generally flat, and includes recessed tubular core attachment feature 35. Although the perimeter of the recessed tubular core attachment feature 35 is shown as rectangular in shape with rounded corners, it will be appreciated that the perimeter shape may be provided in any number of suitable shapes provided that the perimeter shape allows the endplate attachment features 42, 22 to be received therein. The tubular core attachment feature 35 includes a center hole 62. The second surface 34 includes a recess 401 including a shoulder 402 concentrically adjacent the center hole 62. With endplate attachment features 22, 42 positioned within the recessed tubular core attachment feature 35, an endplate lock screw 404, illustrated by way of example in FIG. 37, cooperates with recessed shoulder 402 to fix the endplates 11 to the outer tubular core 14 and the inner tubular core 15.

Figure 39:
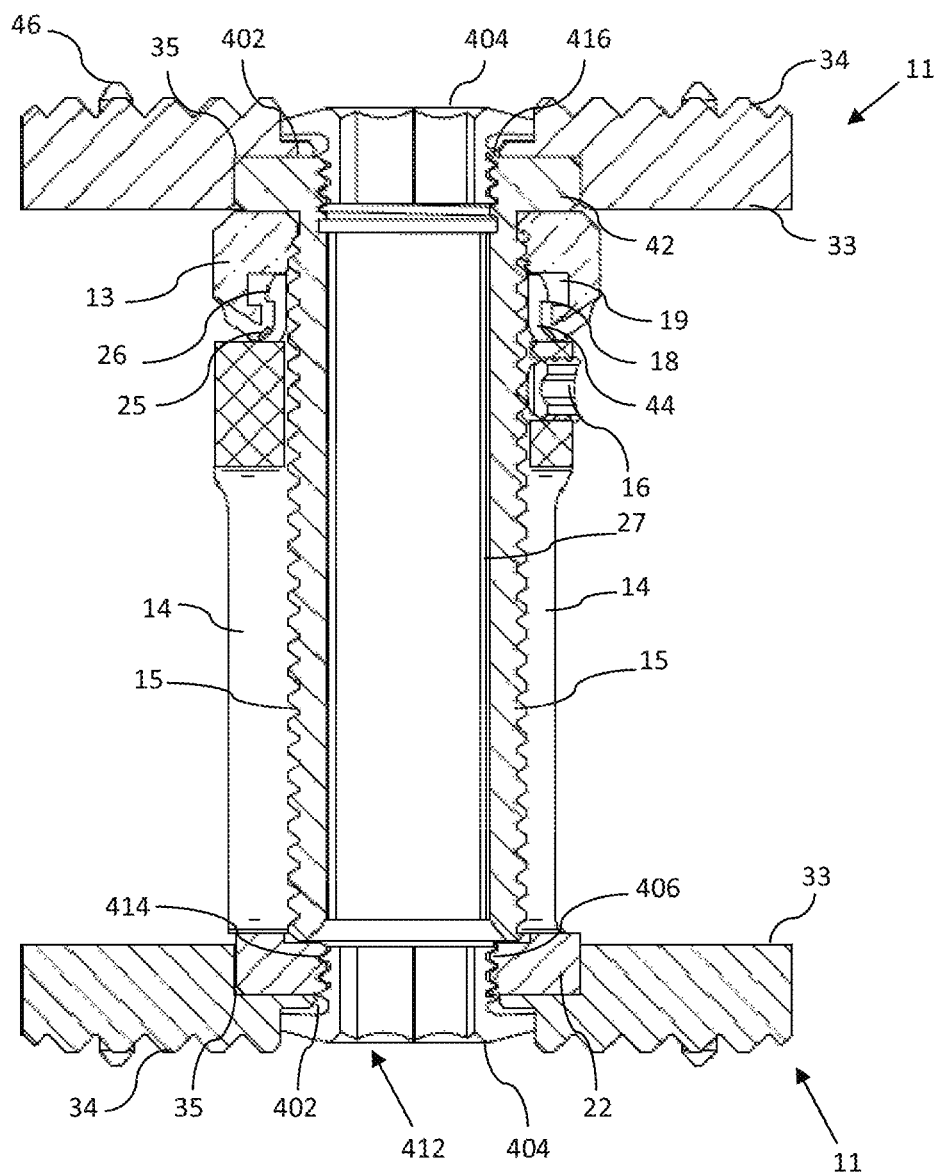
FIG. 39 is a perspective cross section of the implant of FIG. 34.

The endplate lock screw 404 includes a threaded body 406 and a head 410. The threaded body 406 is dimensioned such that it passes through the center hole 62 and engages a complementary threaded region 414, 416 (FIG. 39) within the endplate attachment features 22, 42 of the outer tubular core 14 and inner tubular core 15, respectively. The head 410 is dimensioned such that it fits within the recess 401 and engages shoulder 402 when the threaded body 406 is threaded into the endplate attachment features 42, 22. The lock screw 406 includes a through hole 412 extending all the way through the lock screw. Through hole 412 communicates with the interior of tubular core 12 to permit bone growth between the remaining vertebrae. The sides of through hole 412 are configured with an engagement feature 410 to engage a driver tool (not shown) which is utilized to couple the endplate lock screw 404 to the tubular body 12. By way of example, the engagement feature 410 may be configured to receive a standard hex wrench. According to one example, the engagement feature 410 (and/or the driver tool) may be tapered to create a friction fit between the driver tool and the lock screw 404. The endplate lock screw arrangement of this example embodiment may be advantageous in that it provides for fast and efficient assembly, disassembly, and reassembly. That is, the implant 10 may be assembled intra-operatively according to a first customized selection (e.g. various endplate sizes and/or shape configurations) and then, as needed, easily disassembled and reassembled according to a second customized customization selection.

With reference again to FIG. 34, the adjustment ring 13 of vertebral body implant assembly 400 includes engagement features 418 formed along a beveled side surface 420. By way of example, the side surface may have a 30 degree bevel. The beveled side surface 420 and engagement features 418 cooperate with complementary beveled surfaces of a drive wheel 442 on expansion instrument 430, described below. Also pictured in FIG. 34, are side receptacles 422 positioned within the indented slots 23 of outer tubular core 14 and a center receptacles 424 that enhance the connection between expansion tool 430 and the outer tubular core 14. According to the example shown, center receptacle 424 includes an aperture for receiving set screw 16 to lock the tubular core 12 in the desired position. While a single set screw 16 is shown, it should be appreciated that multiple set screws 16 may be utilized and the outer tubular core 12 may be configured to receive any number of set screws in various arrangements. For example, the outer tubular body 14 could include apertures on either side of the center receptacle 424 in addition to, or in place of, the aperture within the center receptacle in order to receive three or two set screws, respectively.

Figure 40:
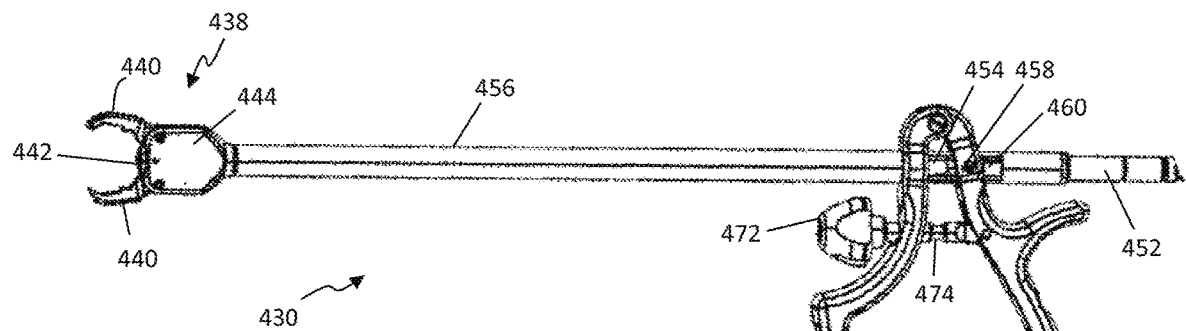
FIG. 40 is a side view of one example of an expansion tool for inserting and expanding the implant of FIG. 34.
Figure 41:
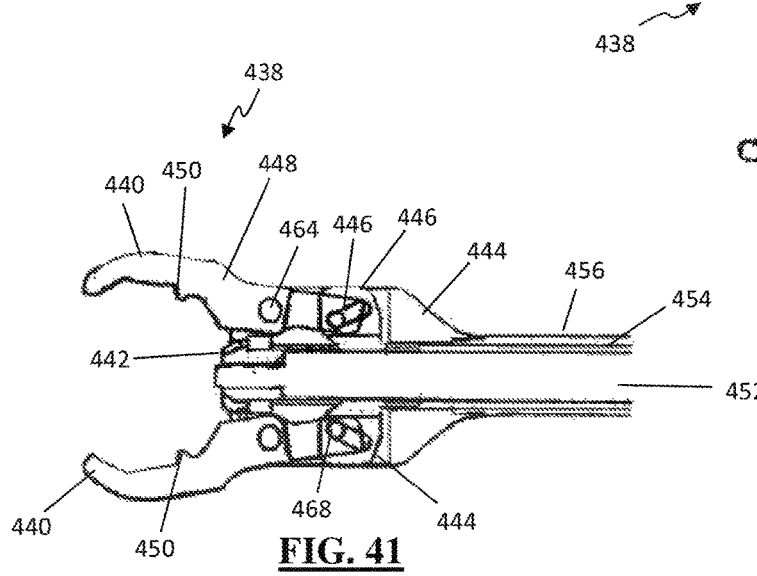
FIG. 41 is a cross section view of the distal end of the expansion tool of FIG. 40.
Figure 42:
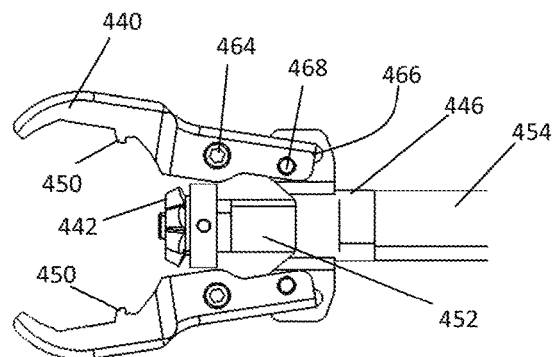
FIG. 42 is a side view of the distal end of the expansion tool of FIG. 41 with the outer housing and outer tube removed for the purposes of illustration.

Turning to FIGS. 40-42, there is shown an example embodiment of an alternate expansion tool 430 for use with the vertebral replacement implant 400. Expanding tool 430 includes a grip 431 having a distal grip 434 and proximal grip 432, a distal engagement region 438, a drive shaft 452, an elongated inner tube 454, and an elongated outer tube 456. Distal engagement region 438 includes a plurality of engagement arms 440, a beveled drive wheel 442, and a housing 444. By way of example only, an engagement arm 440 is composed of a base member 446 and an extension member 448 connected by an angled slot 466 and pin 468. Extension arm 448 is also connected to housing 444 by hinge 464. The engagement arms 440, and particularly the extension member 448, are sized and dimensioned to securely grasp the indented slots 23 of the outer tubular core 14 and secure the position and anti-rotation of the vertebral body implant assembly 400. Ridges 450 on the engagement arms 440 complement and engage with the receptacles 422 located in the indented slots to provide additional stabilization.

The opening (lateral direction) and closing (medial direction) of the engagement arms 440 can be performed by squeezing the grip 431. The proximal grip 432 is fixed to the inner tube 454 by a joint 458 through an opening 460 in the outer tube 456. The distal end of the inner tube 454 meanwhile is fixed to the base members 446 of the engagement arms. The outer tube 456 is fixed at one end to the distal handle 434. At the opposite end the outer tube 456 is fixed to the housing 444. Thus, squeezing the grip 431 causes the proximal handle 432 to translate the inner tube 454 toward the distal end moving the base member 446 distally, which in turn causes the extension arms 448 to rotate around the hinge 464 as the pin 468 moves through angled slot 466. With the engagement arms 440 coupled to the implant 400, a locking mechanism may be engaged to prevent decoupling of the implant. By way of example, the locking mechanism may include a ratchet arm 470 attached to one of the proximal and distal grips. Additionally, or in place of the ratchet arm 470, the locking mechanism may include a threaded nut 472 attached to an arm 474 attached to one of the proximal and distal grips and extending through an opening in the opposite grip.

The drive shaft 452 traverses through the inner tube 454 and is fixed to the beveled drive wheel 442 within housing 44. Rotating the drive shaft 452 causes the beveled drive wheel to rotate in the same direction. Thus, when the expansion tool 430 is fixedly coupled to the implant 400 and the drive shaft 452 is rotated, the drive wheel will impart rotation to the adjustment ring 13, causing expansion of the tubular body 12.

Figure 43A:
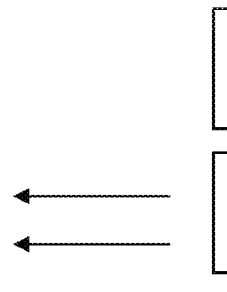
FIG. 43A-43E is a series of side views of the implant assembly of FIG. 1 engaged with the expanding tool of FIG. 23 and the process of implanting the expandable vertebral body between a first vertebra and second vertebra.
Figure 43B:
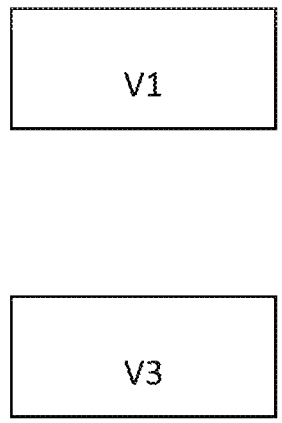
Figure 43C:
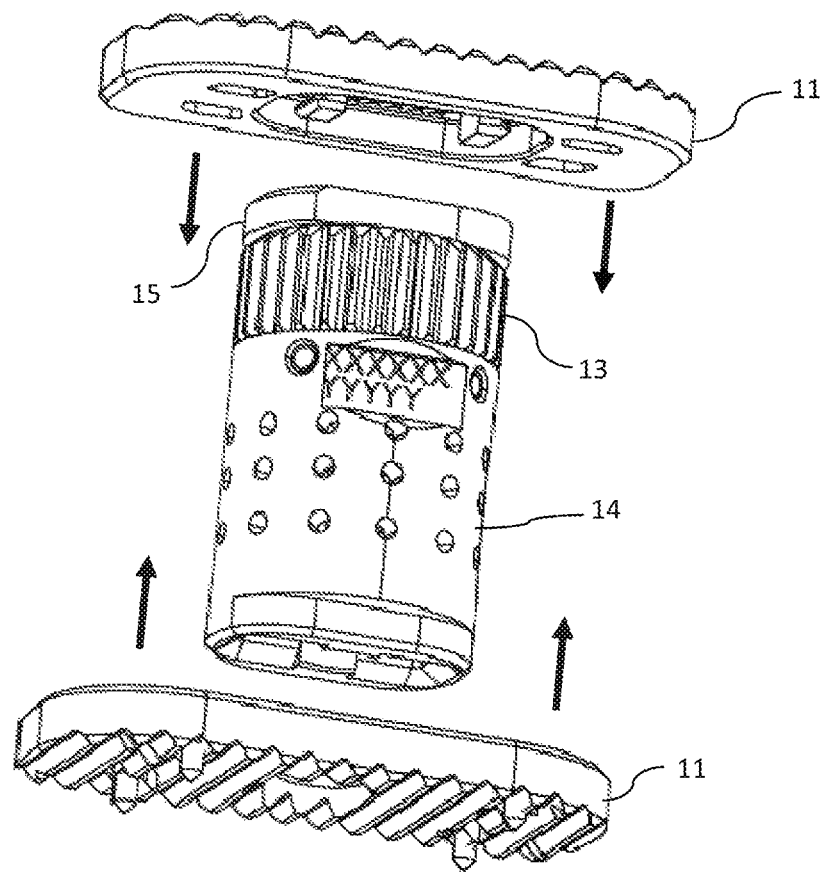

FIG. 43A-43E illustrates one example of a preferred use of a vertebral body implant assembly 10 coupled with an expanding tool 110. While FIGS. 43A-43E picture implant 10 and expanding tool 110, it should be appreciated that the implant 400 and expanding tool 430 may be used according to the same principals while substituting the differences described above. FIG. 43A shows an anterior view of a portion of a spine, which includes a superior vertebra, a medial vertebra and an inferior vertebra which are shown labeled as V1, V2, and V3 respectively. In FIG. 43B, the medial vertebra has been removed so that there is now a large space between the superior and inferior vertebral bodies. In the following figure, FIG. 43C, endplates 11 have been chosen that are preferred for being positioned against the surfaces of the superior and inferior vertebral bodies. These selected endplates 11 are shown being attached (without the use of a loading block 200) at the endplate attachment features 22, 42 of the inner tubular core 15 and outer tubular core 14 of the core expanding body 12. As previously mentioned, a loading block 200 may be used to assist in attaching the endplates to the endplate attachment features 22, 42. The expanding tool 110 can then grasp the indented slots 23 of the outer tubular core 14 by turning the proximal handle 111. This is accomplished by turning the proximal handle 111 one way so that the engagement arms 116 can open and receive the vertebral body implant assembly 10 between the engagement arms 116. Once the core expanding body 12 is positioned between the engagement arms 116, the proximal handle 111 is turned in the opposite direction so that the engagement arms 116 securely grasp the vertebral body implant assembly 10, and preferably so that the engagement arms 116 grasp the vertebral body implant assembly 10 at the general location of the indented slots 23 on the outer tubular core 14.

Figure 43D:
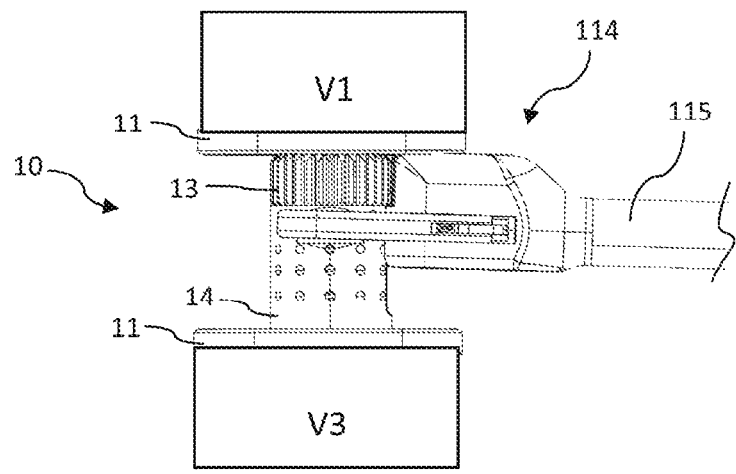
Figure 43E:
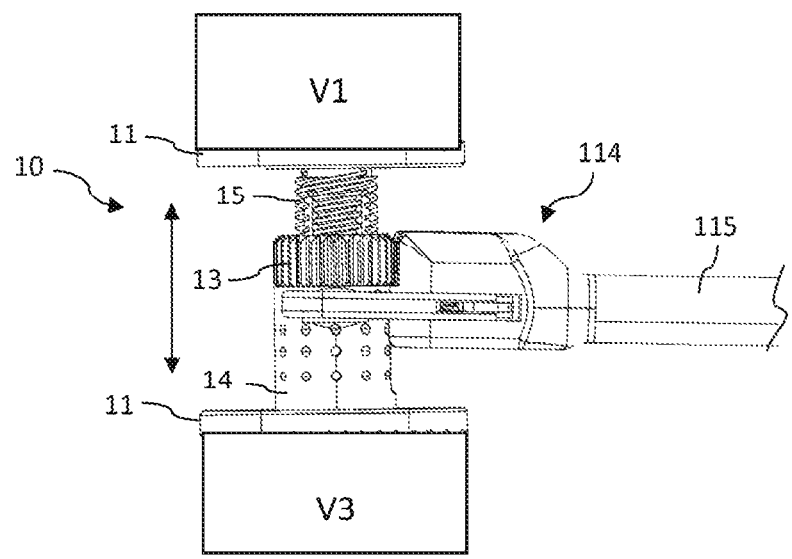

By way of example only, FIG. 43D illustrates the vertebral body implant assembly 10 being inserted in its collapsed state from a lateral direction into the space remaining between the superior and inferior vertebral bodies using the expanding tool 110. The height of the vertebral body implant assembly 10 is then increased by rotating the medial handle 112 which causes the third gear 119 to rotate, as described above. Since the vertebral body implant assembly 10 is secured between the engagement arms 116, the third gear 119 of the expanding tool 110 can engage the external features 21 of the adjustment ring 13 so that when the third gear 119 rotates, it causes the adjustment ring 13 to rotate in concert. As detailed above, rotation of the adjustment ring 13 causes expansion of the vertebral body implant assembly 10, as shown in FIG. 43E. The vertebral body implant assembly 10 is expanded until its desired height has been achieved. It is also possible to rotate the proximal handle 111 in the opposite direction in order to cause the vertebral body implant assembly 10 to decrease in height. Once the desired height has been achieved, the medial handle 112 is rotated in the direction to cause the engagement arms 116 to open and release the vertebral body implant assembly 10. The expanding tool 110 is then separated from the vertebral body implant assembly 10 so that at least one set screw 16 from the outer tubular core 14 can be engaged into the outer wall of the inner tubular core 15 in order to secure the expanded height of the vertebral body implant assembly 10. Additional bone growth promoting material can then be added to the vertebral body implant assembly 10 before it is left to remain implanted between the first and second vertebrae.

While not specifically described above, it will be understood that various other steps may be performed in using and implanting the devices disclosed herein, including but not limited to creating an incision in a patient's skin, distracting and retracting tissue to establish an operative corridor to the surgical target site, advancing the implant through the operative corridor to the surgical target site, removing instrumentation from the operative corridor upon insertion of the implant, and closing the surgical wound.

While this invention has been described in terms of a best mode for achieving this invention's objectives, it will be appreciated by those skilled in the art that variations may be accomplished in view of these teachings without deviating from the spirit or scope of the invention.

What is claimed is:

1. A system comprising:
a vertebral body implant configured to engage a first vertebra and a second vertebra of a spine, wherein the vertebral body implant comprises:
an intermediate expansion member that extends between a first end and a second end along a longitudinal axis and is configured to transition between a collapsed state and an expanded state to adjust a length thereof, and
a first endplate and a second endplate that are configured to couple to the first end and the second end, respectively, of the intermediate expansion member; and
an expansion tool comprising a distal engagement region configured to releasably engage the intermediate expansion member and to adjust the length to a desired length,
wherein the intermediate expansion member comprises:
an outer core having an internal diameter comprising a first plate attachment feature at the first end;
an inner core having an outer diameter comprising a second plate attachment feature at the second end; and
an adjustment ring comprising an attachment feature configured to longitudinally fix the adjustment ring to the outer core, and an internally threaded portion configured to threadably engage an externally threaded portion of the inner core,
wherein the inner core is configured to translate along the longitudinal axis relative to the outer core and the adjustment ring, and
wherein the inner diameter of the outer core is larger than the outer diameter of the inner core.

2. The system of claim 1, wherein the expansion tool further comprises:
an outer tube extending along a second longitudinal axis between a proximal end and a distal end of the expansion tool;
an inner tube disposed within the outer tube and configured to translate along the second longitudinal axis relative to the outer tube; and
a drive shaft disposed within the inner tube and configured to rotate about the second longitudinal axis relative to the inner tube and the outer tube.

3. The system of claim 2, wherein the distal engagement region comprises:
a drive wheel rotatably coupled to the drive shaft and configured to rotatably engage the adjustment ring, thereby adjusting the length to the desired length;
a housing longitudinally fixed to the drive wheel; and
a plurality of engagement arms configured to releasably engage the intermediate expansion member, wherein each engagement arm comprises:
a base member disposed within the housing and coupled to the inner tube, and
an extension member coupled to the housing via a hinge and coupled to the base member via an angled slot and a pin,
wherein the inner tube is configured to displace the base member, which in turn causes the extension member to rotate around the hinge as the pin moves through the angled slot, thereby actuating the plurality of engagement arms to releasably engage the intermediate expansion member.

4. The system of claim 3, wherein the adjustment ring comprises an engagement feature formed along a beveled surface that is configured to rotatably engage the drive wheel.

5. The system of claim 2, wherein the expansion tool further comprises a grip configured to translate the inner tube along the second longitudinal axis relative to the outer tube.

6. The system of claim 5, wherein the grip comprises a distal grip coupled to the outer tube, and a proximal grip coupled to the inner tube,
wherein the proximal grip is configured to distally move toward the distal grip, thereby displacing the inner tube along the second longitudinal axis relative to the outer tube.

7. The system of claim 6, further comprising a locking mechanism configured to inhibit decoupling of the expansion tool and the vertebral body implant.

8. The system of claim 7, wherein the locking mechanism comprises a ratchet arm coupled to at least one of the distal grip and the proximal grip.

9. The system of claim 7, wherein the locking mechanism comprises a threaded nut coupled to one of the distal grip and the proximal grip, and an arm configured to extend through the other one of the distal grip and the proximal grip to threadably engage the threaded nut.

10. The system of claim 1, further comprising:
a first lock screw and a second lock screw that are configured to fix the first endplate and the second endplate, respectively, to the intermediate expansion member; and a driver tool configured to drive the first lock screw and the second lock screw.

11. The system of claim 10, wherein each lock screw comprises a bore configured to communicate with an interior compartment of the intermediate expansion member, thereby permitting bone growth between the first vertebra and the second vertebra.

12. A system comprising:
a vertebral body implant configured to engage a first vertebra and a second vertebra of a spine, wherein the vertebral body implant comprises:
an intermediate expansion member that extends between a first end and a second end along a longitudinal axis and is configured to transition between a collapsed state and an expanded state to adjust a length thereof, and
a first endplate and a second endplate that are configured to couple to the first end and the second end, respectively, of the intermediate expansion member; and
an expansion tool configured to releasably engage the intermediate expansion member and to adjust the length to a desired length, wherein the expansion tool comprises:
a distal engagement region configured to releasably engage the intermediate expansion member,
an outer tube extending along a second longitudinal axis between a proximal end and a distal end of the expansion tool,
an inner tube disposed within the outer tube and configured to translate along the second longitudinal axis relative to the outer tube,
a drive shaft disposed within the inner tube and configured to rotate about the second longitudinal axis relative to the inner tube and the outer tube, and
a grip configured to translate the inner tube along the second longitudinal axis relative to the outer tube,
wherein the distal engagement region comprises:
a drive wheel rotatably coupled to the drive shaft and configured to rotatably engage the intermediate expansion member, thereby adjusting the length thereof to the desired length;
a housing longitudinally fixed to the drive wheel; and
a plurality of engagement arms configured to releasably engage the intermediate expansion member, wherein each engagement arm comprises:
a base member disposed within the housing and coupled to the inner tube, and
an extension member coupled to the housing via a hinge and coupled to the base member via an angled slot and a pin,
wherein the inner tube is configured to displace the base member, which in turn causes the extension member to rotate around the hinge as the pin moves through the angled slot, thereby actuating the plurality of engagement arms to releasably engage the intermediate expansion member.

* * * * *